United States Patent
Kobayashi et al.

(10) Patent No.: US 10,927,389 B2
(45) Date of Patent: Feb. 23, 2021

(54) METHOD OF PRODUCING CHEMICAL SUBSTANCE BY CONTINUOUS FERMENTATION

(71) Applicant: Toray Industries, Inc., Tokyo (JP)

(72) Inventors: Koji Kobayashi, Kamakura (JP); Kenji Sawai, Tokyo (JP); Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 15/303,378

(22) PCT Filed: Apr. 10, 2015

(86) PCT No.: PCT/JP2015/061207
§ 371 (c)(1),
(2) Date: Oct. 11, 2016

(87) PCT Pub. No.: WO2015/159812
PCT Pub. Date: Oct. 22, 2015

(65) Prior Publication Data
US 2017/0037439 A1 Feb. 9, 2017

(30) Foreign Application Priority Data

Apr. 14, 2014 (JP) .................................. 2014-082917
Apr. 14, 2014 (JP) ............................. JP2014-082916

(51) Int. Cl.
*C12P 7/18* (2006.01)
*C12P 7/46* (2006.01)
*C12P 7/02* (2006.01)
*C12P 7/56* (2006.01)
*C12P 7/06* (2006.01)
*C12P 7/16* (2006.01)
*C12P 7/50* (2006.01)
*C12P 7/48* (2006.01)

(52) U.S. Cl.
CPC .................. *C12P 7/56* (2013.01); *C12P 7/06* (2013.01); *C12P 7/16* (2013.01); *C12P 7/18* (2013.01); *C12P 7/46* (2013.01); *C12P 7/48* (2013.01); *C12P 7/50* (2013.01); *Y02E 50/10* (2013.01)

(58) Field of Classification Search
CPC .......... C12P 13/04; C12P 13/08; C12P 19/30; C12P 7/18; C12P 7/42; C12P 7/06; C12P 7/56; C12M 29/04; C12N 15/81; C12N 1/20; C12N 1/16; Y02E 50/17
USPC ... 435/88, 106, 115, 128, 155, 286, 89, 158, 435/161, 136, 146, 142
See application file for complete search history.

(56) References Cited

U.S. PATENT DOCUMENTS

2009/0269812 A1* 10/2009 Sawai et al. ............ C12P 13/04
435/88

FOREIGN PATENT DOCUMENTS

| JP | 2004-344084 A | 12/2004 |
|----|---------------|---------|
| JP | 2009-171879 A | 8/2009 |
| JP | 2010-115112 A | 5/2010 |
| WO | 2007/097260 A1 | 8/2007 |
| WO | 2012/086763 A1 | 6/2012 |
| WO | 2012/147903 A1 | 11/2012 |

OTHER PUBLICATIONS

Matsui et al, Env micro., 2008, p. 4222-4225.*
Endo et al. Biotec biofuels 2008, pp. 1-6.*
Jack DERuiter Princ. Drug action 2005, carboxylic acid part 2 pp. 1-10.*
Makoto Hisamatsu et al., "Isolation and Identification of a Novel Yeast Fermenting Ethanol under Acidic Conditions," J. Appl. Glycosci., vol. 53, 2006, pp. 111-113.
Ayako Endo et al., "Involvement of ergosterol in tolerance to vanillin, a potential inhibitor of bioethanol fermentation, in *Saccharomyces cerevisiae*," FEMS Microbiol. Lett., vol. 299, 2009, pp. 95-99.
Dongxu Cao et al., "Inhibitory Activity of Carbonyl Compounds on Alcoholic Fermentation by *Saccharomyces cerevisiae*," J. Agric. Food Chem., vol. 62, No. 4, Jan. 8, 2014, pp. 918-926 (Abstract).
Sugiyama, M., et al, "Acid Tolerance of Yeast as Classic, Yet New Subject," *The society for Bioscience and Bioengineering*, Japan, Mar. 25, 2009, 87(3), p. 139, along with an English translation.
Nakimura, T., et al., "Development of Yeast for Bioethanol production" *Shokuryo food science and technology*, (51), Mar. 15, 2003, pp. 50-51, along with an English translation.
English translation of the Written Opinion dated Jul. 14, 2015, of corresponding PCT Application No. PCT/JP2015/061207.
Supplementary European Search Report dated Dec. 20, 2017, of corresponding European Application No. 15780585.4.
Chinese First Office Action with Search Report dated Jan. 31, 2019, of counterpart Chinese Application No. 201580019524.8 along with an English translation.

* cited by examiner

*Primary Examiner* — Robert B Mondesi
*Assistant Examiner* — Mohammad Y Meah
(74) *Attorney, Agent, or Firm* — DLA Piper LLP (US)

(57) ABSTRACT

A method of producing a chemical product by continuous fermentation utilizes a separation membrane under conditions at a pH of not more than 3.5, wherein yeast having vanillin resistance is used to enable efficient production of a chemical product without leaving a large amount of fermentation feedstock unused, is provided.

7 Claims, 1 Drawing Sheet

METHOD OF PRODUCING CHEMICAL SUBSTANCE BY CONTINUOUS FERMENTATION

TECHNICAL FIELD

This disclosure relates to a method of producing a chemical product by continuous fermentation under low pH conditions.

BACKGROUND

As the problem of emission of carbon dioxide into the atmosphere and the energy problem have become obvious, biomass-derived chemical products represented by biodegradable polymer materials such as lactic acid, and biofuels such as ethanol, have been drawing strong attention because of the sustainability and the life cycle assessment (LCA)-oriented nature of such products.

When an organic acid such as lactic acid is to be produced by a microorganism, the pH of the culture liquid decreases due to the organic acid produced, leading to a decrease in the productivity of the organic acid of interest. The pH of the culture liquid therefore needs to be kept constant using a neutralizer. For example, JP 2009-171879 A discloses a method of producing lactic acid by culture of a yeast, wherein the pH of the culture liquid is maintained by alkaline neutralization to maintain the lactic acid productivity of the yeast. However, when the medium is neutralized using an alkaline substance such as calcium hydroxide, depending on the amount of the alkaline substance added, by-products such as gypsum may be produced in the later separation/purification step due to the influence of an acidic substance such as sulfuric acid which is added for separation of lactic acid salt. This makes the step of separation/purification of lactic acid complicated, and increases the production cost as a result. That is, when a neutralizer is used, additional cost is required not only for the raw material of the neutralizer itself, but also for removal/disposal of the unnecessary by-products such as gypsum. Also for organic acids other than lactic acid, neutralizers such as sodium hydroxide are used for keeping the pH of the culture liquid constant during the culture. Thus, organic acid production using yeasts, which are more resistant to low pH than bacteria, is being studied. This is because, since yeasts can be cultured at lower pH than bacteria, the amount of the neutralizer used can be reduced. In addition, improvement of microorganisms having resistance to lower pH is being carried out. For example, JP 2010-115112 A and WO 2012/147903 A1 disclose methods of producing lactic acid using mutant strains having lactic acid resistance.

Production of chemical products other than organic acids such as ethanol is also carried out at low pH in some cases. JP 2004-344084 A, for example, describes elimination of the necessity of pH adjustment when ethanol fermentation by a yeast is carried out using, as a raw material, a sugar liquid produced by hydrolyzing a biomass resource using an acid such as sulfuric acid, and also describes that, since the risk of contamination with unwanted microorganisms can be reduced at low pH, sterilization of the medium and the fermentation apparatus becomes unnecessary in such cases.

Examples of common culture methods for microorganisms include batch culture, fed-batch culture, and continuous culture. WO 2007/097260 A1 discloses improvement of the production rate and the yield of a fermentation product by continuous culture using a separation membrane.

As mentioned above, WO '260 discloses a method of producing lactic acid or ethanol by continuous fermentation using a separation membrane while the pH of the culture liquid is kept at 5, which method uses, as a lactic acid fermentation microorganism, the *Saccharomyces cerevisiae* NBRC 10505 strain in which a lactate dehydrogenase gene is introduced in the chromosome, or, as an ethanol fermentation microorganism, the NBRC 10505 strain. In the above method, continuous production of lactic acid or ethanol is carried out without leaving the fermentation feedstock, sugar, unused.

However, we discovered another problem that, when continuous fermentation using a separation membrane is carried out in the same manner as in WO '260 under low pH conditions (at a pH of not more than 3.5), the sugar consumption becomes very slow, and a large amount of sugar is not consumed and remains unused. If a large amount of fermentation feedstock such as sugar remains unused, the yield of the product relative to the fermentation feedstock fed for the fermentation decreases. In such a case, the cost is adversely affected since, for example, the cost of the product increases, and removal of the fermentation feedstock in the later purification step is very laborious.

SUMMARY

We discovered that, in a method of producing a chemical product by continuous fermentation using a separation membrane, the above problem can be solved by using a yeast having resistance to vanillin.

We thus provide in (1) to (5) below:

(1) A method of producing a chemical product, the method comprising filtering a culture liquid of yeast through a separation membrane while retaining or refluxing unfiltered liquid in the culture liquid, and adding a fermentation feedstock to the culture liquid, to perform continuous fermentation under conditions at a pH of not more than 3.5, wherein, as the yeast, yeast whose culture liquid obtained under the following Conditions (a) shows an absorbance at 600 nm of not less than 20% of the absorbance at 600 nm of a culture liquid obtained under the following Conditions (b) is used:

Conditions (a): 40 hours of culture in YPAD medium supplemented with vanillin (final concentration, 1 g/L) (absorbance at 600 nm at the beginning of the culture, 0.2);

Conditions (b): culture under the same conditions as in Conditions (a) except that the YPAD medium does not contain vanillin.

(2) The method of producing a chemical product according to (1), wherein, as the yeast, yeast whose culture liquid obtained under the Conditions (a) shows an absorbance at 600 nm of not less than 50% of the absorbance at 600 nm of a culture liquid obtained under the Conditions (b) is used.

(3) The method of producing a chemical product according to (1) or (2), wherein, as the yeast, yeast whose culture liquid obtained under the following Conditions (c) shows an absorbance at 600 nm of not less than 20% of the absorbance at 600 nm of a culture liquid obtained under the following Conditions (d) is used:

Conditions (c): 40 hours of culture in YPAD medium supplemented with 4% (v/v) acetone (absorbance at 600 nm at the beginning of the culture, 0.2);

Conditions (d): culture under the same conditions as in Conditions (c) except that the YPAD medium does not contain acetone.

(4) The method of producing a chemical product according to any one of (1) to (3), wherein the feed rate of the fermentation feedstock is not less than 4 g/(L·hr).

(5) The method of producing a chemical product according to any one of (1) to (4), wherein the chemical product is an organic acid or an alcohol.

A chemical product can be efficiently produced in continuous fermentation using a separation membrane even under conditions at a pH of not more than 3.5, without leaving a large amount of fermentation feedstock unused in the filtrate.

DETAILED DESCRIPTION

Figure 1:
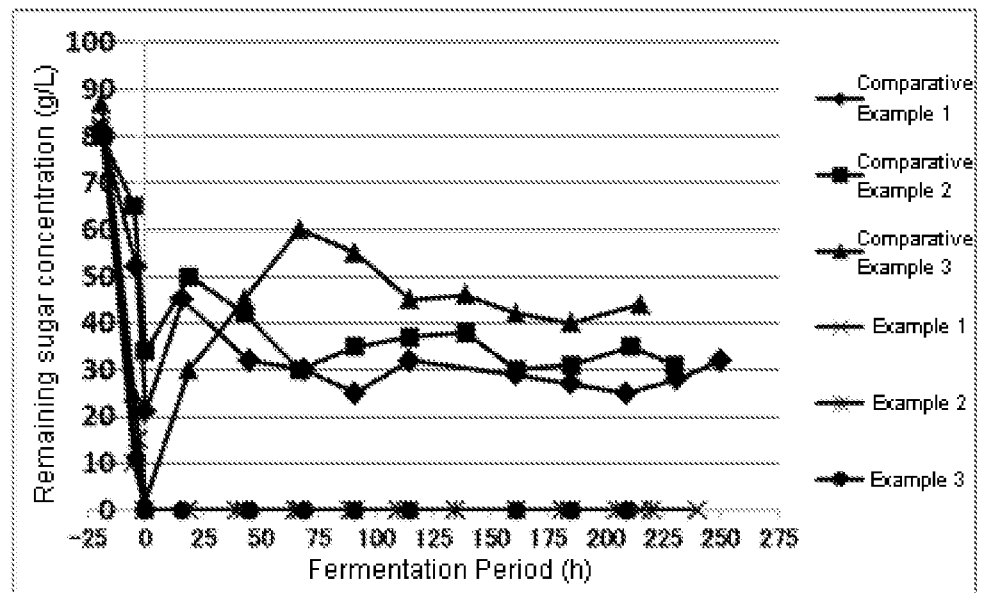
FIG. 1 shows the remaining sugar concentration in the culture liquid during the preculture, and the remaining sugar concentration in the filtrate from the beginning to the completion of the continuous fermentation using a separation membrane, in Comparative Examples 1 to 3 and Examples 1 to 3. Hour 0 represents the time when the continuous fermentation using a separation membrane was started, and the period before Hour 0 corresponds to the preculture period (for 19 hours).

The yeast used in our method is described below.

The yeast having resistance to vanillin (hereinafter referred to as vanillin-resistant yeast) is characterized in that, as a result of a test in which the absorbance of a culture liquid obtained under the following Conditions (a) is compared with the absorbance of a culture liquid obtained under the following Conditions (b) (hereinafter referred to as vanillin resistance test), the absorbance of the culture liquid obtained under Conditions (a) is not less than 20% of the absorbance of the culture liquid obtained under Conditions (b). The ratio is preferably not less than 30%, more preferably not less than 40%, still more preferably not less than 50%, still more preferably not less than 60%, especially preferably not less than 70%, most preferably not less than 80%.

Conditions (a): 40 hours of culture in YPAD medium supplemented with vanillin (final concentration, 1 g/L) (absorbance at 600 nm at the beginning of the culture, 0.2).

Conditions (b): culture under the same conditions as in Conditions (a) except that the YPAD medium does not contain vanillin.

By an unknown mechanism, a vanillin-resistant yeast can produce a chemical product even in continuous fermentation using a separation membrane at a pH of not more than 3.5, without leaving a large amount of fermentation feedstock unused. "Leaving a large amount of fermentation feedstock unused" means a state where the fermentation feedstock has not been consumed and remains in the filtrate obtained by filtration of the culture liquid through the separation membrane. If a large amount of fermentation feedstock remains unused in the filtrate, the yield of the product relative to the fermentation feedstock fed for the fermentation decreases. In such a case, the cost of the product increases, and, moreover, the burden of removal of the fermentation feedstock in the later purification increases. Thus, the smaller the amount of the fermentation feedstock remaining in the filtrate, the better.

The conditions (a) and (b) in the vanillin resistance test are described below in detail. In the conditions (a) and (b), the absorbance at 600 nm at the beginning of the culture is adjusted to 0.2 (OD 600 nm=0.2). Examples of its method include, but are not limited to, a method in which yeast cells are grown by preculture, and the absorbance of the culture liquid is measured, followed by controlling the amount of the cells to be inoculated to the main culture liquid such that OD 600 nm=0.2 is achieved, and a method in which the cells are grown on an agar plate, and the amount of the cells to be inoculated from the agar plate is controlled such that OD 600 nm=0.2 is achieved.

As the medium for the culture in the vanillin resistance test, YPAD medium is used. The YPAD medium used herein is a medium having the following composition: 1% (w/v) yeast extract, 2% (w/v) bactopeptone, 2% (w/v) glucose, and 0.04% (w/v) adenine.

In the preparation of the YPAD medium supplemented with vanillin (final concentration, 1 g/L), which is used under Conditions (a), a vanillin concentrate is preferably added to sterilized YPAD medium. The vanillin concentrate is preferably prepared at 100 to 200 g/L, most preferably prepared at 200 g/L. This is because the influence of the organic solvent for dissolving vanillin on the growth should be reduced as much as possible. As the organic solvent to dissolve vanillin, DMSO is preferably used. For example, if a vanillin concentrate (200 g/L) is prepared, the YPAD medium supplemented with vanillin may be prepared by adding 25 µl of the vanillin concentrate to 5 ml of YPAD medium. To the vanillin-free YPAD medium, 25 µl of DMSO alone is preferably added. This is because the influence of DMSO on the growth should be taken into account.

The vanillin-resistant yeast preferably also has resistance to acetone. When a yeast having vanillin resistance as well as acetone resistance is used, the fermentation feedstock remaining in the filtrate obtained by the continuous fermentation using a separation membrane at a pH of not more than 3.5 can be further reduced so that more efficient production of a chemical product is possible.

The yeast having resistance to acetone (hereinafter referred to as acetone-resistant yeast) is characterized in that, as a result of a test in which the absorbance of a culture liquid obtained under the following Conditions (c) is compared with the absorbance of a culture liquid obtained under the following Conditions (d) (hereinafter referred to as acetone resistance test), the absorbance of the culture liquid obtained under Conditions (c) is not less than 20% of the absorbance of the culture liquid obtained under Conditions (d). The ratio is preferably not less than 30%, more preferably not less than 40%, still more preferably not less than 50%, still more preferably not less than 60%, still more preferably not less than 70%, still more preferably not less than 80%.

Conditions (c): 40 hours of culture in YPAD medium supplemented with 4% (v/v) acetone (absorbance at 600 nm at the beginning of the culture, 0.2).

Conditions (d): culture under the same conditions as in Conditions (c) except that the YPAD medium does not contain acetone.

The conditions (c) and (d) in the acetone resistance test are described below in detail. In the conditions (c) and (d), the absorbance at 600 nm at the beginning of the culture is adjusted to 0.2 (OD 600 nm=0.2).

As the medium for the culture in the acetone resistance test, YPAD medium is used.

In the preparation of the YPAD medium supplemented with 4% (v/v) acetone, which is used under Conditions (c), acetone is preferably added to sterilized YPAD medium.

The culture temperatures for Conditions (a) to (d) are not limited as long as sufficient growth of the yeast cells is possible. The culture temperatures are preferably 28 to 30° C., more preferably 30° C.

The spectrophotometer used for the measurement of the absorbances of the culture liquids obtained under Conditions (a) to (d) is not limited. However, the same spectrophotometer needs to be used for Conditions (a) to (d).

The vanillin-resistant yeast (and vanillin-resistant as well as acetone-resistant yeast) can be selected by screening by a vanillin resistance test (and an acetone resistance test) from yeast strains known to those skilled in the art. Specific examples of such a yeast include the *Saccharomyces cerevisiae* NBRC 2260 strain, *Kluyveromyces marxianus* NBRC 272 strain, *Candida tropicalis* NBRC 199 strain, *Arxula adeninivorans* NBRC 10858 strain, *Lindnera fabianii* NBRC 1253 strain, *Candida methanosorbosa* BCRC 21489 strain, *Pichia stipitis* BCRC 21777 strain, and *Candida boidinii* BCRC 22528 strain. Of course, a yeast prepared by subjecting a yeast having no vanillin resistance (or acetone resistance) to a mutation treatment known to those skilled in the art such that the result of a vanillin resistance test (or an acetone resistance test) becomes not less than 20% also corresponds to the vanillin-resistant yeast (or the vanillin-resistant as well as acetone-resistant yeast) in the present description.

The method of producing a chemical product by continuous fermentation using a separation membrane is described below.

As the fermentation feedstock to be used in the method of producing a chemical product, either a natural medium or a synthetic medium may be used as long as it contains a carbon source, nitrogen source, inorganic salt, and/or the like that can be metabolized by the yeast, and as long as it allows efficient culture of the yeast. More specifically, in terms of the carbon source, it is preferred to use, as a major component(s) of the fermentation feedstock, one or more kinds of the so-called sugars selected from the group consisting of carbohydrates such as glucose, fructose, sucrose, galactose, maltose, raffinose, trehalose, sorbose, cellobiose, lactose, melibiose, melezitose, inulin, xylose, arabinose, ribose, rhamnose, glucosamine, erythritol, ribitol, mannitol, glucitol, salicin, starch, and starch, and hydrolysates thereof; and saccharified liquids obtained from cellulose and the like derived from biomass. Carbon sources such as organic acids including acetic acid, propionic acid, and citric acid; and alcohols including ethanol and propanol; may also be used as major components of the fermentation feedstock. Specific examples of the nitrogen source that may be used include: ammonia; ammonium salts of inorganic acids and organic acids such as ammonium chloride, ammonium sulfate, ammonium acetate, and ammonium phosphate; other nitrogen-containing compounds; peptone; meat extracts; and corn steep liquors. Examples of the inorganic substance that may be used include potassium dihydrogenphosphate, magnesium phosphate, magnesium sulfate, sodium chloride, ferrous sulfate, manganese sulfate, copper sulfate, and calcium carbonate. These carbon sources, nitrogen sources, inorganic salts, and the like may be added at once upon the start of culture, or may be added separately or continuously during the culture.

When the yeast requires a particular nutrient for its growth, the nutrient may be added as a preparation or a natural product containing it. An anti-forming agent may also be added as required.

The culture liquid means a liquid obtained as a result of metabolism of a fermentation feedstock during the growth of a microorganism. The composition of the fermentation feedstock to be added may be changed as appropriate from the fermentation feedstock composition at the beginning of the culture so that the production of the chemical product of interest increases.

When a sugar(s) is/are used as a major component(s) of the fermentation feedstock, the total sugar concentration is not limited, and preferably as high as possible within the range in which the production of the chemical product by the yeast is not inhibited. More specifically, the total sugar concentration is preferably 15 to 500 g/L, more preferably 20 to 300 g/L.

The production efficiency of a chemical product can be evaluated based on the yield of the chemical product produced with respect to the major component of the fermentation feedstock metabolized by the microorganism. The yield is evaluated as the value calculated according to Equation (1):

$$\text{Yield (g/g)} = \text{total amount of product (g)} \div \{\text{total amount of fermentation feedstock fed (g)} - \text{unused fermentation feedstock (g)}\} \times 100 \qquad (1).$$

The total amount of fermentation feedstock fed herein represents the total amount of the major component of the fermentation feedstock fed for the fermentation, and the unused fermentation feedstock represents the total amount of the major component of the fermentation feedstock that has not been consumed and is remaining until the completion of the fermentation. More specifically, in cases of batch fermentation, the unused fermentation feedstock represents the major component of the fermentation feedstock that has not been metabolized by the microorganism and is remaining in the culture liquid until the completion of the fermentation. In cases of continuous fermentation, the unused fermentation feedstock represents the major component of the fermentation feedstock remaining in the filtrate after filtration of the culture liquid through a separation membrane. The total amount of product is the total amount of the chemical product produced (g).

The feed rate of the fermentation feedstock during the continuous fermentation is not limited. The feed rate is preferably not less than 4 g/(L·hr). This is because, when the feed rate of the fermentation feedstock is lower than this, the effect of suppressing remaining of the fermentation feedstock may be deteriorated. The feed rate of the fermentation feedstock is calculated according to Equation (2):

$$\text{Feed rate of fermentation feedstock (g/(L·hr))} = \text{fermentation feedstock concentration in medium (g/L)} \times \text{feed rate of fermentation feedstock to fermenter (L/hr)} \div \text{operational liquid volume of apparatus (L)} \qquad (2).$$

The separation membrane is not limited as long as it has a function to separate, by filtration, a culture liquid obtained by culturing a microorganism in a stirred culture vessel or a stirred bioreactor from the microorganism. Examples of the separation membrane include porous ceramic membranes, porous glass membranes, porous organic polymer membranes, metal fiber textiles, and non-woven fabrics. Among these, porous organic polymer membranes and ceramic membranes are especially preferred.

The separation membrane is preferably a separation membrane having a porous resin layer from the viewpoint of the blocking performance, permeability, and separation performance, for example, resistance to dirt.

The separation membrane having a porous resin layer preferably has a porous resin layer that acts as a separation function layer, on a surface of a porous base material. The porous base material supports the porous resin layer to give strength to the separation membrane.

When the separation membrane has a porous resin layer on a surface of a porous base material, the porous base material may be impregnated with the porous resin layer, or may not be impregnated with the porous resin layer, depending on the use.

The average thickness of the porous base material is preferably 50 μm to 3000 μm.

The porous base material is composed of an organic material inorganic material, and/or the like. An organic fiber is preferably used. The porous base material is preferably a woven fabric or non-woven fabric composed of an organic fiber such as a cellulose fiber, cellulose acetate fiber, polyester fiber, polypropylene fiber, or polyethylene fiber. The porous base material is more preferably a non-woven fabric since its density can be relatively easily controlled, and it can be easily produced.

As the porous resin layer, an organic polymer membrane may be favorably used. Examples of the material of the organic polymer membrane include polyethylene resins, polypropylene resins, polyvinyl chloride resins, polyvinylidene fluoride resins, polysulfone resins, polyethersulfone resins, polyacrylonitrile resins, cellulose resins, and cellulose triacetate resins. The organic polymer membrane may also be a mixture of resins containing two or more of these resins as major components. The major component means that the component is contained in an amount of not less than 50% by weight, preferably not less than 60% by weight. The material of the organic polymer membrane is preferably a polyvinyl chloride resin, polyvinylidene fluoride resin, polysulfone resin, polyethersulfone resin, or polyacrylonitrile resin. A polyvinylidene fluoride resin or a resin containing it as a major component is most preferably used.

As the polyvinylidene fluoride resin, a homopolymer of vinylidene fluoride is preferably used. The polyvinylidene fluoride resin is also preferably a copolymer with vinyl monomers capable of copolymerizing with vinylidene fluoride. Examples of the vinyl monomers capable of copolymerizing with vinylidene fluoride include tetrafluoroethylene, hexafluoropropylene, and trifluoroethylene chloride.

The separation membrane is not limited as long as it does not allow passing of the microorganism used in the fermentation. Preferably, the separation membrane is less likely to undergo fouling due to secretions of the microorganism used in the fermentation and fine particles in the fermentation feedstock, and stably maintains its filtration performance for a long time. Thus, the average pore size of the separation membrane is preferably not less than 0.01 μm and less than 5 μm. When the average pore size of the separation membrane is not less than 0.01 μm and less than 1 μm, both a high blocking rate which does not allow leakage of the microorganism and a high permeability can be achieved, and the permeability can be maintained with high accuracy and reproducibility for a long time.

The average pore size of the separation membrane is preferably less than 1 μm since, when the average pore size is close to the size of the microorganism, the pores may be directly clogged with the microorganism. From the viewpoint of preventing leakage of the microorganism, that is, preventing occurrence a trouble causing a decrease in the elimination rate, the average pore size of the separation membrane is preferably not too large relative to the size of the microorganism. When small cells such as bacterial cells are used as the microorganism, the average pore size is preferably not more than 0.4 μm. The filtration can be more favorably carried out in cases where the average pore size is less than 0.2 μm.

In some cases, the microorganism produces substances other than the desired chemical product such as proteins and polysaccharides that are prone to aggregation, and cell debris may be produced by death of a part of the microorganism in the fermentation culture liquid. To avoid clogging of the separation membrane with such substances, the average pore size is still more preferably not more than 0.1 μm.

When the average pore size of the separation membrane is too small, the permeability of the separation membrane may be low so that its efficient operation is impossible even without fouling of the membrane. The average pore size of the separation membrane is therefore preferably not less than 0.01 μm, more preferably not less than 0.02 μm, still more preferably not less than 0.04 μm.

The average pore size can be determined by measuring the diameters of all pores which can be observed within an area of 9.2 μm×10.4 μm under the scanning electron microscope at a magnification of 10,000×, and averaging the measured values. Alternatively, the average pore size can be determined by taking a picture of the surface of the membrane using a scanning electron microscope at a magnification of 10,000×, and randomly selecting not less than 10, preferably not less than 20 pores, followed by measuring the diameters of these pores and calculating the number average. When a pore is not circular, a circle having the same area as that of the pore (equivalent circle) may be determined using an image processing device or the like, and the diameter of the equivalent circle may be regarded as the diameter of the pore.

The standard deviation σ of the average pore size of the separation membrane is preferably not more than 0.1 μm. The smaller the standard deviation σ of the average pore size, the better. The standard deviation σ of the average pore size is calculated according to Equation (3), wherein N represents the number of pores observable within the above-mentioned area of 9.2 μm×10.4 μm; Xk represents the respective measured diameters; and X(ave) represents the average of the pore sizes.

$$\sigma = \sqrt{\frac{\sum_{k=1}^{N}(X_k - X(ave))^2}{N}} \quad (3)$$

In the separation membrane, permeability to the fermentation culture liquid is one of its important properties. As an index for permeability of the separation membrane, the pure water permeability coefficient of the separation membrane before use can be used. The pure water permeability coefficient of the separation membrane is preferably not less than $5.6 \times 10^{-10}$ m$^3$/m$^2$/s/pa as calculated when the amount of permeation is measured at a temperature of 25° C. with a head height of 1 m using purified water prepared by filtration through a reverse osmosis membrane. When the pure water permeability coefficient is from $5.6 \times 10^{-10}$ m³/m²/s/pa to $6 \times 10^{-7}$ m³/m²/s/pa, an amount of permeation which is practically sufficient can be obtained.

The membrane surface roughness of the separation membrane is the average height in the vertical direction from the surface. The membrane surface roughness is a factor which enables easy detachment of the microorganism adhering to the surface of the separation membrane, by the membrane surface washing effect of a liquid current produced by stirring or a circulating pump. The surface roughness of the separation membrane is not limited as long as the microorganism and other solids adhering to the membrane can be detached. The surface roughness is preferably not more than 0.1 µm. When the surface roughness is not more than 0.1 µm, the microorganism and other solids adhering to the membrane can be easily detached.

The separation membrane more preferably has a surface roughness of not more than 0.1 µm, average pore size of not less than 0.01 µm and less than 1 µm, and pure water permeability coefficient of not less than $2 \times 10^{-9}$ m³/m²/s/pa. We found that, by using such a membrane, the operation can be more easily carried out without requiring excessive power for washing the membrane surface. When the membrane surface roughness is not more than 0.1 µm, the shear force generated on the membrane surface during the filtration of the microorganism can be reduced, and destruction of the microorganism can therefore be suppressed so that fouling of the separation membrane can be suppressed. Thus, stable filtration can be more easily carried out for a long time. When the membrane surface roughness of the separation membrane is not more than 0.1 µm, continuous fermentation can be carried out with a smaller transmembrane pressure difference and, even when fouling of the separation membrane occurred, the membrane can be more easily recovered by washing compared to cases where the operation was carried out with a large transmembrane pressure difference. Since stable continuous fermentation is possible by suppressing fouling of the separation membrane, the surface roughness of the separation membrane is preferably as small as possible.

The membrane surface roughness of the separation membrane is measured using the following atomic force microscope (AFM) under the following conditions:
Apparatus
Atomic force microscope apparatus ("Nanoscope IIIa," manufactured by Digital Instruments)
Conditions
Probe: SiN cantilever (manufactured by Digital Instruments)
Scanning mode: Contact mode (measurement in air)
Underwater tapping mode (underwater measurement)
Scanning area: 10 µm×10 µm, 25 µm×25 µm (measurement in air)
5 µm×5 µm, 10 µm×10 µm (underwater measurement)
Scanning resolution: 512×512
Sample Preparation
For the measurement, the membrane sample was soaked in ethanol at room temperature for 15 minutes, and then soaked in RO water for 24 hours, followed by washing and drying it in the air. The RO water means water prepared by filtration through a reverse osmosis membrane (RO membrane), which is a separation membrane, to remove impurities such as ions and salts. The pore size of the RO membrane is not more than about 2 nm.

The membrane surface roughness, drough, is calculated according to Equation (4) using the above atomic force microscope apparatus (AFM), based on the heights of respective points in the direction of the z-axis.

$$d_{rough} = \sum_{n=1}^{N} \frac{|Z_n - \overline{Z}|}{N} \qquad (4)$$

$d_{rough}$: Average surface roughness (µm)

$Z_n$: Height in the direction of the z-axis (µm)

$\overline{Z}$: Average height in the scanning area (µm)

The separation membrane is preferably in the shape of a flat membrane. When the separation membrane is in the shape of a flat membrane, its average thickness is selected depending on the use. When the separation membrane is in the shape of a flat membrane, its average thickness is preferably 20 µm to 5000 µm, more preferably 50 µm to 2000 µm.

Alternatively, the separation membrane is preferably in the shape of a hollow fiber membrane. When the separation membrane is a hollow fiber membrane, the inner diameter of the hollow fiber is preferably 200 µm to 5000 µm, and the membrane thickness is preferably 20 µm to 2000 µm. A fabric or a knit produced by forming an organic fiber or an inorganic fiber into a cylindrical shape may be contained in the hollow fiber.

The separation membrane mentioned above can be produced by, for example, the production method described in WO 2007/097260.

Preferably, the separation membrane may be a membrane containing at least a ceramic. The ceramic means a ceramic which contains a metal oxide and is sintered by heat treatment at high temperature. Examples of the metal oxide include alumina, magnesia, titania, and zirconia. The separation membrane may be formed with the metal oxide alone, or may contain silica; silicon carbide; and/or a compound of silica and a metal oxide(s) such as mullite or cordierite.

Components other than the ceramic forming the separation membrane are not limited as long as they allow formation of a porous body as the separation membrane.

Also, when the separation membrane contains a ceramic, the shape of the separation membrane is not limited, and any of, for example, monolith membranes, flat membranes, and tubular membranes may be employed. From the viewpoint of efficient filling into a container, the separation membrane preferably has a columnar structure wherein penetrating holes are formed in the longitudinal direction. From the viewpoint of increasing the filling efficiency, the separation membrane is preferably a monolith membrane.

The reason why the penetrating holes are preferably formed in the longitudinal direction is as follows. When a separation membrane having a columnar shape is placed in a module container to provide a separation membrane module, a preferred mode of the separation membrane may be selected from external-pressure type membranes and internal-pressure type membranes, and the separation membrane in this mode may be used to provide the module to be used for the filtration. The side of the separation membrane contacting the fermentation culture liquid is hereinafter referred to as the primary side, and the side in which the filtrate containing a chemical product is obtained by the filtration is hereinafter referred to as the secondary side.

When an internal-pressure type module is used, the primary-side channel is narrow so that the output of the circulating pump can be saved when cross-flow filtration is carried out. Moreover, since the action to discharge the suspended matter deposited on the surface of the separation membrane increases, the surface of the separation membrane is likely to be kept clean, which is preferred. However, to obtain this effect, the internal-pressure type separation membrane needs to have an inlet and an outlet for the fermentation culture liquid. When the inlet and the outlet are in the state of penetrating holes that are linearly arranged, the flow resistance can be reduced, which is preferred. When the separation membrane has a columnar structure wherein penetrating holes are open in the longitudinal direction, a thin container can be used for containing the separation membrane. A thin separation membrane module can be favorably used from the viewpoint of its production and ease of handling.

Although the porosity of the separation membrane is not limited, a low porosity leads to a low filtration efficiency, while a high porosity leads to a low strength. To achieve both a favorable filtration efficiency and a favorable strength of the separation membrane, and to give resistance to repeated steam sterilization, the porosity is preferably 20% to 60%.

The porosity is determined according to Equation (5):

Porosity [%]=100×(wet membrane weight [g]−dry membrane weight [g]) specific gravity of water [g/cm$^3$]/(membrane volume [cm$^3$])  (5)

The average pore size of the separation membrane is preferably 0.01 μm to 1 μm. When the membrane has an average pore size within this range, clogging of the separation membrane is less likely to occur, and an excellent filtration efficiency can be achieved. When the average pore size is within the range of 0.02 μm to 0.2 μm, substances that often cause clogging of the separation membrane, for example, by-products of fermentation by the microorganism or cultured cells such as proteins and polysaccharides, and cell debris produced by death of the microorganism/cultured cells in the culture liquid, become less likely to cause clogging, which is especially preferred.

In a separation membrane with a columnar shape in which penetrating holes are formed, the outer surface corresponds to the secondary side. Such a separation membrane is therefore preferably used as a module in which a module container that collects the filtrate is provided, and the module container is loaded with the separation membrane. One or more separation membranes are placed in a module.

The module container is preferably composed of a material resistant to repeated steam sterilization treatment. Examples of the material resistant to steam sterilization treatment include stainless steels and ceramics with low average porosities.

Such a ceramic membrane module can be produced by the production method described in WO2012/086763. Alternatively, a commercially available product may be used. Specific examples of the commercially available product include an MEMBRALOX microfiltration membrane (Pall) and a ceramic membrane filter Cefilt MF membrane (NGK Insulators, Ltd.).

The continuous fermentation is characterized in that a culture liquid of yeast is filtered through a separation membrane while unfiltered liquid is retained or refluxed in the culture liquid; a fermentation feedstock is added to the culture liquid; and the product is recovered from the filtrate.

The transmembrane pressure difference during the filtration through the separation membrane is not limited as long as filtration of the fermentation culture liquid is possible. However, when filtration treatment to filter the culture liquid is carried out using an organic polymer membrane with a transmembrane pressure difference of more than 150 kPa, the structure of the organic polymer membrane is likely to be destroyed, and this may lead to low capacity to produce the chemical product. On the other hand, with a transmembrane pressure difference of as low as less than 0.1 kPa, the amount of permeation of the fermentation culture liquid is often insufficient so that the productivity in production of the chemical product tends to be low. Thus, in the method of producing a chemical product, in an organic polymer membrane, the transmembrane pressure difference as the filtration pressure is preferably 0.1 kPa to 150 kPa. Under such conditions, the amount of permeation of the fermentation culture liquid is large, and there is no lowering of the capacity to produce the chemical product due to destruction of the membrane structure so that the capacity to produce the chemical product can be kept high. In organic polymer membranes, the transmembrane pressure difference is preferably 0.1 kPa to 50 kPa, more preferably 0.1 kPa to 20 kPa.

The temperature during the fermentation by the yeast may be a temperature suitable for the yeast used, and is not limited as long as it is within the range in which the microorganism can grow. The fermentation is carried out at a temperature of 20 to 75° C.

The pH of the culture liquid during the continuous fermentation is adjusted to not more than 4. The pH of the culture liquid is adjusted in advance with an inorganic or organic acid, alkaline substance, urea, calcium carbonate, ammonia gas, or the like to a predetermined pH of not more than 4.

In the method of producing a chemical product, batch culture or fed-batch culture may be carried out in the initial phase of the culture to increase the microorganism concentration and, after this, continuous culture (filtration of the culture liquid) may be started. Alternatively, microbial cells at high concentration may be seeded, and continuous culture may be started at the beginning of culture. In the method of producing a chemical product, it is possible to start supply of the medium and filtration of the culture liquid at appropriate timings. The times to start the supply of the medium and filtration of the culture liquid do not necessarily need to be the same. The supply of the medium and the filtration of the culture liquid may be carried out either continuously or intermittently.

The concentration of the microorganism in the culture liquid is preferably kept such that the productivity of the chemical product is high, from the viewpoint of obtaining efficient productivity. For example, when the concentration of the microorganism in the culture liquid is kept at not less than 5 g/L in terms of dry weight, a favorable production efficiency can be obtained.

If necessary, during the continuous fermentation, a part of the culture liquid containing the microorganism may be removed from the fermenter, and the culture liquid may then be diluted with a medium to control the concentration of the microorganism in the fermenter. For example, since, if the concentration of the microbial cells in the fermenter is too high, clogging of the separation membrane is likely to occur, the clogging can be prevented in some cases by removing a part of the culture liquid containing the microorganism and diluting the culture liquid with a medium. Since the performance to produce the chemical product may change depending on the concentration of the microorganism in the fermenter, the productive performance can be maintained by using the productive performance as an index for the removal of a part of the culture liquid containing the microorganism and the dilution of the culture liquid with a medium.

In the method of producing a chemical product, the number of fermenters is not limited as long as the method is continuous culture which produces the product while allowing the growth of microbial cells.

The continuous fermentation apparatus is not limited as long as it is an apparatus for production of a chemical product by continuous fermentation in which a fermentation culture liquid of yeast is filtered through a separation membrane to recover the product from the filtrate, while unfiltered liquid is retained or refluxed in the fermentation culture liquid; a fermentation feedstock is added to the fermentation culture liquid; and the product in the filtrate is recovered. When an organic polymer membrane is used, specific examples of the continuous fermentation apparatus include the apparatus described in WO 2007/097260.

The produced chemical product is not limited as long as it is a chemical product which can be produced by a yeast known to those skilled in the art (including yeasts subjected to mutation treatment or genetic recombination). Preferred examples of the chemical product include organic acids and alcohols. Specific examples of the organic acids include acetic acid, lactic acid, adipic acid, pyruvic acid, succinic acid, malic acid, itaconic acid, and citric acid. Specific examples of the alcohols include ethanol, 1,3-propanediol, 1,3-butanediol, 2,3-butanediol, 1,4-butanediol, glycerol, butanol, isobutanol, 2-butanol, and isopropanol. These chemical products are recovered from the filtrate by a well-known method(s) (membrane separation, concentration, distillation, crystallization, extraction, and/or the like).

EXAMPLES

Our methods are described below more concretely by way of Examples. However, this disclosure is not limited to the Examples.

Reference Example 1: Method of Analyzing Glucose and Ethanol

The concentrations of glucose and ethanol in the culture liquid were quantified under the HPLC conditions described below, based on comparison with standard samples:
  Column: Shodex SH1011 (manufactured by Showa Denko K. K.)
  Mobile phase: 5 mM sulfuric acid (flow rate, 0.6 mL/minute)
  Reaction solution: none
  Detection method: RI (differential refractive index)
  Temperature: 65° C.

Reference Example 2: Method of Analyzing Lactic Acid

Lactic acid in the fermentation liquid was quantified under the HPLC conditions described below based on comparison with standard samples:
  Column: Shim-Pack SPR-H (manufactured by Shimadzu Corporation)
  Mobile phase: 5 mM p-toluenesulfonic acid (flow rate, 0.8 mL/min.)
  Reaction solution: 5 mM p-toluenesulfonic acid, 20 mM Bis-Tris, 0.1 mM EDTA-2Na (flow rate, 0.8 mL/min.)
  Detection method: electric conductivity
  Temperature: 45° C.

Reference Example 3: Introduction of D-Lactate Dehydrogenase Gene into PDC1 Locus in Saccharomyces cerevisiae NBRC 10505 Strain As the D-lactate dehydrogenase gene (D-LDH), one derived from *Limulus polyphemus* (see WO 2010/140602) was used. Examples of the method of inserting DNA containing the D-LDH gene into the downstream of the promoter for the PDC1 gene in the chromosome by homologous recombination include, but are not limited to, a method in which PCR is carried out using primers for the upstream and the downstream of the DNA containing the D-LDH gene, which primers are designed such that portions homologous to the target site of introduction are added, and the resulting PCR fragment is used for transformation of the yeast. For simple selection of transformants, the PCR fragment preferably contains a yeast selection marker such as an amino acid synthetase gene or a drug resistance gene.

The transformation was carried out by the lithium acetate method using the "YEASTMAKER Yeast Transformation System" (manufactured by CLONETECH). For details of the operation, the manufacturer's instructions were followed. The *Saccharomyces cerevisiae* NBRC 10505 strain as the host is a strain which lacks the capacity to synthesize tryptophan, and, by the action of the TRP1 gene, transformants to which the gene is introduced can be selected on a tryptophan-free medium.

Introduction of the D-LDH gene into the thus obtained transformants was confirmed by extracting genomic DNA containing plasmid DNA from the transformants cultured in YPAD medium using a genomic DNA extraction kit "Dr. GenTLE" (manufactured by TAKARA BIO INC.), and then performing PCR with the extracted DNA as a template using "PreMix Taq" (manufactured by TAKARA BIO INC.). As a result, we confirmed that all transformants have the D-LDH gene inserted in the PDC1 locus.

The *Saccharomyces cerevisiae* NBRC 10505 strain having the D-LDH derived from *Limulus polyphemus* at the PDC1 locus, obtained in the above process, is hereinafter referred to as the NBRC 10505/ΔPDC1::LDH strain.

Reference Example 4: Introduction of D-Lactate Dehydrogenase Gene into PDC1 Locus in Saccharomyces cerevisiae NBRC 2260 Strain As the D-lactate dehydrogenase gene (D-LDH), one derived from *Limulus polyphemus* (see WO 2010/140602) was used. The *Saccharomyces cerevisiae* NBRC 2260 strain to be used as the host is a strain with no amino acid auxotrophy. By using a resistance gene against a drug such as Geneticin (G418) or Hygromycin, transformants to which the D-LDH gene is introduced can be selected on a medium supplemented with the drug. Using G418 as a selection marker, transformation was carried out by the same method as in Reference Example 3. For the transformants obtained, the introduction of the D-LDH gene was confirmed by the same method as in Reference Example 3. As a result, we confirmed that all transformants have the D-LDH gene inserted in the PDC1 locus.

The *Saccharomyces cerevisiae* NBRC 2260 strain having the D-LDH derived from *Limulus polyphemus* at the PDC1 locus, obtained in the above process, is hereinafter referred to as the NBRC 2260/ΔPDC1::LDH strain.

Reference Example 5: Vanillin Resistance Test and Acetone Resistance Test of *Saccharomyces cerevisiae* NBRC 10505 Strain Vanillin Resistance Test The *Saccharomyces cerevisiae* NBRC 10505 strain was inoculated using a platinum loop to 20-ml test tubes each containing 5 ml of YPAD medium, and then cultured with shaking at 30° C. overnight (preculture). The YPAD medium had the following composition: 1% (w/v) yeast extract, 2% (w/v) bactopeptone, 2% (w/v) glucose, and 0.04% (w/v) adenine. A vanillin concentrate (200 g/L in DMSO) was prepared, and 25 µL of the vanillin concentrate was added to 5 ml of YPAD medium so that the final concentration became 1 g/L. To provide vanillin-free YPAD medium, 25 µl of DMSO alone was added to YPAD medium. The preculture liquid was inoculated to the YPAD medium (with vanillin) and the vanillin-free YPAD medium such that OD became 0.2, and culture was performed at 30° C. for 40 hours. After the culture, OD 600 nm of the culture liquid of each strain was measured, and a value was calculated according to Equation (6). The calculated value is shown in Table 1.

Absorbance at 600 nm of YPAD medium (with vanillin)÷absorbance at 600 nm of YPAD medium×100   (6).

As a result, the *Saccharomyces cerevisiae* NBRC 10505 strain was found to be a yeast which does not have vanillin resistance.

Acetone Resistance Test

The *Saccharomyces cerevisiae* NBRC 10505 strain was inoculated using a platinum loop to 20-ml test tubes each containing 5 ml of YPAD medium, and then cultured with shaking at 30° C. overnight (preculture). The YPAD medium had the following composition: 1% (w/v) yeast extract, 2% (w/v) bactopeptone, 2% (w/v) glucose, and 0.04% (w/v) adenine. To 5 ml of YPAD medium, 200 µL of acetone was added so that the final concentration became 4% (v/v). The preculture liquid was inoculated to the YPAD medium (with acetone) and the acetone-free YPAD medium such that OD 600 nm became 0.2, and culture was performed at 30° C. for 40 hours. After the culture, OD 600 nm of the culture liquid of each strain was measured, and a value was calculated according to Equation (7). The calculated value is shown in Table 1.

Absorbance at 600 nm of YPAD medium (with acetone)÷absorbance at 600 nm of YPAD medium×100   (7)

As a result, the *Saccharomyces cerevisiae* NBRC 10505 strain was found to be a yeast which does not have acetone resistance.

Reference Example 6: Vanillin Resistance Test and Acetone Resistance Test of *Candida pignaliae* NBRC 10307 Strain The *Candida pignaliae* NBRC 10307 strain was tested by the same method as in Reference Example 5, and values were calculated according to Equation (6) and Equation (7) (Table 1). As a result, the *Candida pignaliae* NBRC 10307 strain was found to be a yeast having neither vanillin resistance nor acetone resistance.

Reference Example 7: Vanillin Resistance Test of *Pichia mexicana* NBRC 10320 Strain The *Pichia mexicana* NBRC 10320 strain was tested by the same method as in Reference Example 5, and values were calculated according to Equation (6) and Equation (7) (Table 1). As a result, the *Pichia mexicana* NBRC 10320 strain was found not to be a vanillin-resistant yeast, but found to be an acetone-resistant yeast.

Reference Example 8: Vanillin Resistance Test and Acetone Resistance Test of *Saccharomyces cerevisiae* NBRC 2260 Strain The *Saccharomyces cerevisiae* NBRC 2260 strain was tested by the same method as in Reference Example 5, and values were calculated according to Equation (6) and Equation (7) (Table 1). As a result, the *Saccharomyces cerevisiae* NBRC 2260 strain was found to be a vanillin-resistant as well as acetone-resistant yeast.

Reference Example 9: Vanillin Resistance Test and Acetone Resistance Test of *Kluyveromyces marxianus* NBRC 272 Strain The *Kluyveromyces marxianus* NBRC 272 strain was tested by the same method as in Reference Example 5, and values were calculated according to Equation (6) and Equation (7) (Table 1). As a result, the *Kluyveromyces marxianus* NBRC 272 strain was found to be a vanillin-resistant as well as acetone-resistant yeast.

Reference Example 10: Vanillin Resistance Test and Acetone Resistance Test of *Candida tropicalis* NBRC 199 Strain The *Candida tropicalis* NBRC 199 strain was tested by the same method as in Reference Example 5, and values were calculated according to Equation (6) and Equation (7) (Table 1). As a result, the *Candida tropicalis* NBRC 199 strain was found to be a vanillin-resistant as well as acetone-resistant yeast.

Reference Example 11: Vanillin Resistance Test and Acetone Resistance Test of *Arxula adeninivorans* NBRC 10858 Strain The *Arxula adeninivorans* NBRC 10858 strain was tested by the same method as in Reference Example 5, and values were calculated according to Equation (6) and Equation (7) (Table 1). As a result, the *Arxula adeninivorans* NBRC 10858 strain was found to be a vanillin-resistant as well as acetone-resistant yeast.

Reference Example 12: Vanillin Resistance Test and Acetone Resistance Test of *Lindnera fabianii* NBRC 1253 Strain The *Lindnera fabianii* NBRC 1253 strain was tested by the same method as in Reference Example 5, and a value was calculated according to Equation (6) and Equation (7) (Table 1). As a result, the *Lindnera fabianii* NBRC 1253 strain was found to be a vanillin-resistant as well as acetone-resistant yeast.

Reference Example 13: Vanillin Resistance Test and Acetone Resistance Test of *Candida methanosorbosa* BCRC 21489 Strain The *Candida methanosorbosa* BCRC 21489 strain was tested by the same method as in Reference Example 5, and values were calculated according to Equation (6) and Equation (7) (Table 1). As a result, the *Candida methanosorbosa* BCRC 21489 strain was found to be a vanillin-resistant as well as acetone-resistant yeast.

Reference Example 14: Vanillin Resistance Test and Acetone Resistance Test of *Pichia stipitis* BCRC 21777 Strain The *Pichia stipitis* BCRC 21777 strain was tested by the same method as in Reference Example 5, and values were calculated according to Equation (6) and Equation (7) (Table 1). As a result, the *Pichia stipitis* BCRC 21777 strain was found to be a vanillin-resistant yeast, but found not to be an acetone-resistant yeast.

Reference Example 15: Vanillin Resistance Test and Acetone Resistance Test of *Candida boidinii* BCRC 22528 Strain The *Candida boidinii* BCRC 22528 strain was tested by the same method as in Reference Example 5, and values were calculated according to Equation (6) and Equation (7) (Table 1). As a result, the *Candida boidinii* BCRC 22528 strain was found to be a vanillin-resistant as well as acetone-resistant yeast.

tested by the same method as in Reference Example 5, and values were calculated according to Equation (6) and Equation (7) (Table 2). As a result, the *Saccharomyces cerevisiae* NBRC 2260/ΔPDC1::LDH strain was found to be a vanillin-resistant as well as acetone-resistant yeast.

Reference Example 18: Vanillin Resistance Test and Acetone Resistance Test of *Saccharomyces cerevisiae* NITE BP-1087 Strain The *Saccharomyces cerevisiae* NITE BP-1087 strain, which is a low-pH-resistant yeast strain described in WO 2012/147903, was tested by the same method as in Reference Example 5, and values were calculated according to Equation (6) and Equation (7) (Table 2). As a result, the NITE BP-1087 strain was found to be a yeast having neither vanillin resistance nor acetone resistance.

Reference Example 19: Vanillin Resistance Test and Acetone Resistance Test of *Saccharomyces cerevisiae* NITE BP-1088 Strain The *Saccharomyces cerevisiae* NITE BP-1088 strain, which is a low-pH-resistant yeast strain described in WO 2012/147903, was tested by the same method as in Refer-

TABLE 1

Vanillin resistance test results 1 (ethanol fermentation microorganism)

|  | Reference Example 5 | Reference Example 6 | Reference Example 7 | Reference Example 8 | Reference Example 9 | Reference Example 10 |
|---|---|---|---|---|---|---|
| Strain name | NBRC 10505 | NBRC 10307 | NBRC 10320 | NBRC 2260 | NBRC 272 | NBRC 199 |
| Vanillin resistance test result | 6.8 | 1.9 | 11 | 83 | 100 | 82 |
| Acetone resistance test result | 8.8 | 1.3 | 100 | 86 | 87 | 100 |

|  | Reference Example 11 | Reference Example 12 | Reference Example 13 | Reference Example 14 | Reference Example 15 |
|---|---|---|---|---|---|
| Strain name | NBRC 10858 | NBRC 1253 | BCRC 21489 | BCRC 21777 | BCRC 22528 |
| Vanillin resistance test result | 84 | 95 | 54 | 22 | 66 |
| Acetone resistance test result | 22 | 111 | 74 | 1.8 | 49 |

Reference Example 16: Vanillin Resistance Test and Acetone Resistance Test of *Saccharomyces cerevisiae* NBRC 10505/ΔPDC1::LDH Strain The *Saccharomyces cerevisiae* NBRC 10505/ΔPDC1::LDH strain, which is a lactic acid fermentation yeast, was tested by the same method as in Reference Example 5, and values were calculated according to Equation (6) and Equation (7) (Table 2). As a result, the *Saccharomyces cerevisiae* NBRC 10505/ΔPDC1::LDH strain was found to be a yeast having neither vanillin resistance nor acetone resistance.

Reference Example 17: Vanillin Resistance Test and Acetone Resistance Test of *Saccharomyces cerevisiae* NBRC 2260/ΔPDC1::LDH Strain The *Saccharomyces cerevisiae* NBRC 2260/ΔPDC1::LDH strain, which is a lactic acid fermentation yeast, was ence Example 5, and values were calculated according to Equation (6) and Equation (7) (Table 2). As a result, the NITE BP-1088 strain was found to be a yeast having neither vanillin resistance nor acetone resistance.

Reference Example 20: Vanillin Resistance Test and Acetone Resistance Test of *Saccharomyces cerevisiae* NITE BP-1089 Strain The *Saccharomyces cerevisiae* NITE BP-1089 strain, which is a low-pH-resistant yeast strain described in WO 2012/147903, was tested by the same method as in Reference Example 5, and values were calculated according to Equation (6) and Equation (7) (Table 2). As a result, the NITE BP-1089 strain was found to be a yeast having neither vanillin resistance nor acetone resistance.

TABLE 2

Vanillin resistance test results 2 (lactic acid fermentation microorganism)

| | Reference Example 16 | Reference Example 17 | Reference Example 18 | Reference Example 19 | Reference Example 20 |
|---|---|---|---|---|---|
| Strain name | NBRC 10505 ΔPDC1::LDH strain | NBRC 2260 ΔPDC1::LDH strain | BP-1087 | BP-1088 | BP-1089 |
| Vanillin resistance test result | 6.2 | 82 | 9.2 | 8.5 | 7.8 |
| Acetone resistance test result | 8 | 84 | 10 | 7.5 | 7.2 |

Reference Example 21: Production of Ethanol by Batch Fermentation (pH 3) by *Saccharomyces cerevisiae* NBRC 10505 Strain As an ethanol fermentation microorganism, the *Saccharomyces cerevisiae* NBRC 10505 strain, which is a yeast having neither vanillin resistance nor acetone resistance, was used and, as a medium, YPAD medium for continuous fermentation, containing glucose as a major component of the fermentation feedstock, was used. The YPAD medium for continuous fermentation had the following composition: 1% (w/v) yeast extract, 2% (w/v) bactopeptone, 8% (w/v) glucose, and 0.04% (w/v) adenine. The *Saccharomyces cerevisiae* NBRC 10505 strain was inoculated in 5 mL of the preculture medium shown in Table 3 in a test tube, and cultured with shaking overnight (pre-preculture). The obtained culture liquid was inoculated in 50 ml of a fresh preculture medium, and subjected to culture in a 500-ml Sakaguchi flask for 8 hours at a temperature of 30° C. with shaking (preculture). The preculture liquid was inoculated in 2 L of the YPAD medium for continuous fermentation (whose pH was adjusted to 3.5 using 4 N KOH before the inoculation), and batch fermentation was carried out under the following conditions (table 4). The yield was calculated according to Equation (1). As a result, we confirmed that, in the batch fermentation (pH 3) by the *Saccharomyces cerevisiae* NBRC 10505 strain, ethanol can be produced without leaving sugar unused.

Fermentation reaction vessel capacity: 2 (L)
Temperature adjustment: 30(° C.)
Aeration rate in the fermentation reaction vessel: 50 (mL/min.)
Stirring rate in the fermentation reaction vessel: 400 (rpm)
pH adjustment: adjusted to pH 3 with 4 N KOH
Sterilization: the culture vessel and all media were autoclaved at 121° C. for 20 minutes.

TABLE 3

Preculture medium

| | |
|---|---|
| Glucose | 100 g |
| Yeast Nitrogen base w/o amino acid (Difco) | 6.7 g |
| Yeast Synthetic Drop-out Medium Supplement without Tryptophan | 1.72 g |
| Tryptophan | 76 mg |
| Adenine | 76 mg |

Unit (1/Liter)

Reference Example 22: Production of Ethanol by Batch Fermentation (pH 3) by *Candida pignaliae* NBRC 10307 Strain As an ethanol fermentation microorganism, the *Candida pignaliae* NBRC 10307 strain, which is a yeast having neither vanillin resistance nor acetone resistance, was used to perform batch fermentation under the same conditions as in Reference Example 21, to produce ethanol (Table 4). As a result, we confirmed that, in the batch fermentation (pH 3) by the *Candida pignaliae* NBRC 10307 strain, ethanol can be produced without leaving sugar unused.

Reference Example 23: Production of Ethanol by Batch Fermentation (pH 3) by *Pichia mexicana* NBRC 10320 Strain As an ethanol fermentation microorganism, the *Pichia mexicana* NBRC 10320 strain, which is not a vanillin-resistant yeast, but is an acetone-resistant yeast, was used to perform batch fermentation under the same conditions as in Reference Example 21, to produce ethanol (Table 4). As a result, we confirmed that, in the batch fermentation (pH 3) by the *Pichia mexicana* NBRC 10320 strain, ethanol can be produced without leaving sugar unused.

Reference Example 24: Production of Ethanol by Batch Fermentation (pH 3) by *Saccharomyces cerevisiae* NBRC 2260 Strain As an ethanol fermentation microorganism, the *Saccharomyces cerevisiae* NBRC 2260 strain, which is a vanillin-resistant as well as acetone-resistant yeast, was used to perform batch fermentation under the same conditions as in Reference Example 21, to produce ethanol (Table 4). As a result, we confirmed that, in the batch fermentation (pH 3) by the *Saccharomyces cerevisiae* NBRC 2260 strain, ethanol can be produced without leaving sugar unused.

Reference Example 25: Production of Ethanol by Batch Fermentation (pH 3) by *Kluyveromyces marxianus* NBRC 272 Strain As an ethanol fermentation microorganism, the *Kluyveromyces marxianus* NBRC 272 strain, which is a vanillin-resistant as well as acetone-resistant yeast, was used to perform batch fermentation under the same conditions as in Reference Example 21, to produce ethan-ol (Table 4). As a result, we confirmed that, in the batch fermentation (pH 3) by the *Kluyver-omyces marxianus* NBRC 272 strain, ethanol can be produced without leaving sugar unused.

Reference Example 26: Production of Ethanol by Batch Fermentation (pH 3) by *Candida tropicalis* NBRC 199 Strain As an ethanol fermentation microorganism, the *Candida tropicalis* NBRC 199 strain, which is a vanillin-resistant as well as acetone-resistant yeast, was used to perform batch fermentation under the same conditions as in Reference Example 21, to produce ethanol (Table 4). As a result, we confirmed that, in the batch fermentation (pH 3) by *Candida tropicalis* NBRC 199 strain, ethanol can be produced without leaving sugar unused.

Reference Example 27: Production of Ethanol by Batch Fermentation (pH 3) by *Arxula adeninivorans* NBRC 10858 Strain As an ethanol fermentation microorganism, the *Arxula adeninivorans* NBRC 10858 strain, which is a vanillin-resistant as well as acetone-resistant yeast, was used to perform batch fermentation under the same conditions as in Reference Example 21, to produce ethanol (Table 4). As a result, we confirmed that, in the batch fermentation (pH 3) by the *Arxula adeninivorans* NBRC 10858 strain, ethanol can be produced without leaving sugar unused.

Reference Example 28: Production of Ethanol by Batch Fermentation (pH 3) by *Lindnera fabianii* NBRC 1253 Strain As an ethanol fermentation microorganism, the *Lindnera fabianii* NBRC 1253 strain, which is a vanillin-resistant as well as acetone-resistant yeast, was used to perform batch fermentation under the same conditions as in Reference Example 21, to produce ethanol (Table 4). As a result, we confirmed that, in the batch fermentation (pH 3) by the *Lindnera fabianii* NBRC 1253 strain, ethanol can be produced without leaving sugar unused.

Reference Example 29: Production of Ethanol by Batch Fermentation (pH 3) by *Candida methanosorbosa* BCRC 21489 Strain As an ethanol fermentation microorganism, the *Candida methanosorbosa* BCRC 21489 strain, which is a vanillin-resistant as well as acetone-resistant yeast, was used to perform batch fermentation under the same conditions as in Reference Example 21, to produce ethanol (Table 4). As a result, we confirmed that, in the batch fermentation (pH 3) by the *Candida methanosorbosa* BCRC 21489 strain, ethanol can be produced without leaving sugar unused.

Reference Example 30: Production of Ethanol by Batch Fermentation (pH 3) by *Pichia stipitis* BCRC 21777 Strain As an ethanol fermentation microorganism, the *Pichia stipitis* BCRC 21777 strain, which is a vanillin-resistant yeast, but not an acetone-resistant yeast, was used to perform batch fermentation under the same conditions as in Reference Example 21, to produce ethanol (Table 4). As a result, we confirmed that, in the batch fermentation (pH 3) by the *Pichia stipitis* BCRC 21777 strain, ethanol can be produced without leaving sugar unused.

Reference Example 31: Production of Ethanol by Batch Fermentation (pH 3) by *Candida boidinii* BCRC 22528 Strain As an ethanol fermentation microorganism, the *Candida boidinii* BCRC 22528 strain, which is a vanillin-resistant as well as acetone-resistant yeast, was used to perform batch fermentation under the same conditions as in Reference Example 21, to produce ethanol (Table 4). As a result, we confirmed that, in the batch fermentation (pH 3) by the *Candida boidinii* BCRC 22528 strain, ethanol can be produced without leaving sugar unused.

TABLE 4

| Ethanol fermentation results 1 (batch fermentation, pH 3) | | | | | | |
|---|---|---|---|---|---|---|
| | Reference Example 21 | Reference Example 22 | Reference Example 23 | Reference Example 24 | Reference Example 25 | Reference Example 26 |
| Culture period (hr) | 25 | 28 | 20 | 15 | 18 | 16 |
| Total amount of glucose fed (g) | 80 | 80 | 80 | 80 | 80 | 80 |
| Total production of ethanol (g) | 33 | 32 | 33 | 34 | 33 | 33 |
| Unused glucose (g) | 0 | 0 | 0 | 0 | 0 | 0 |
| Yield (g/g) | 0.41 | 0.4 | 0.41 | 0.42 | 0.41 | 0.41 |
| | Reference Example 27 | Reference Example 28 | Reference Example 29 | Reference Example 30 | Reference Example 31 | |
| Culture period (hr) | 20 | 19 | 16 | 22 | 20 | |
| Total amount of glucose fed (g) | 80 | 80 | 80 | 80 | 80 | |
| Total production of ethanol (g) | 33 | 33 | 33 | 32 | 33 | |
| Unused glucose (g) | 0 | 0 | 0 | 0 | 0 | |
| Yield (g/g) | 0.41 | 0.41 | 0.41 | 0.4 | 0.41 | |

Comparative Example 1: Production of Ethanol by Continuous Fermentation (pH 3) by *Saccharomyces cerevisiae* NBRC 10505 Strain Using Separation Membrane As an ethanol fermentation microorganism, the *Saccharomyces cerevisiae* NBRC 10505 strain, which is a yeast having neither vanillin resistance nor acetone resistance, was used, and, as a medium, YPAD medium for continuous fermentation containing glucose as a major component of the fermentation feedstock, which is the same medium as in Reference Example 21, was used, to perform continuous culture using a separation membrane. A separation membrane element having a hollow-fiber shape was employed. The YPAD medium for continuous fermentation had the following composition: 1% (w/v) yeast extract, 2% (w/v)

bactopeptone, 8% (w/v) glucose, and 0.04% (w/v) adenine. The *Saccharomyces cerevisiae* NBRC 10505 strain was inoculated in 5 mL of the preculture medium shown in Table 2 in a test tube, and cultured with shaking overnight (pre-pre-preculture). The obtained culture liquid was inoculated in 50 ml of a fresh preculture medium, and subjected to culture in a 500-ml Sakaguchi flask for 8 hours at a temperature of 30° C. with shaking (pre-preculture). The pre-preculture liquid was inoculated in 1.5 L of the YPAD medium for continuous fermentation (whose pH was adjusted to 3 using 4 N KOH before the inoculation) in a continuous fermentation apparatus, and culture was performed for 19 hours while the fermentation reaction vessel was stirred at 400 rpm using the stirrer attached, and the aeration rate, temperature, and pH in the fermentation reaction vessel were controlled (preculture). After completion of the preculture, operation of a fermentation liquid circulation pump and continuous supply of the medium were immediately started, and continuous culture was performed for 250 hours under the following conditions while the amount of the culture liquid filtered was controlled such that the fermentation liquid volume in the continuous fermentation apparatus was 1.5 L, to produce ethanol (Table 5). The yield was calculated according to Equation (1).

Fermentation reaction vessel capacity: 2 (L)
Separation membrane used: polyvinylidene fluoride filtration membrane
Effective filtration area of the membrane separation element: 473 (cm$^2$)
Temperature adjustment: 30(° C.)
Aeration rate in the fermentation reaction vessel: 50 (mL/min.)
Stirring rate in the fermentation reaction vessel: 400 (rpm)
pH adjustment: adjusted to pH 3 with 4 N KOH
Fermentation liquid removal rate: 5.5 (L/Day)
Sterilization: the culture vessel including the separation membrane element, and all media were autoclaved at 121° C. for 20 minutes.

The membrane used has the following properties. The transmembrane pressure difference during the filtration was changed within the range of 0.1 to 19.8 kPa.

Average pore size: 0.1 µm
Standard deviation of the average pore size: 0.035 µm
Membrane surface roughness: 0.06 µm
Pure water permeability coefficient: 50×10$^{-9}$ m$^3$/m$^2$/s/pa FIG. 1 shows the remaining sugar concentration in the culture liquid during the preculture, and the remaining sugar concentration in the filtrate from the beginning to the completion of the continuous fermentation using the separation membrane. As a result, we found that, in the continuous fermentation (pH 3) by the *Saccharomyces cerevisiae* NBRC 10505 strain using the separation membrane, a large amount of sugar that had not been consumed during the continuous fermentation was left unused in the filtrate so that the production efficiency was low.

Comparative Example 2: Production of Ethanol by Continuous Fermentation (pH 3) by *Candida pignaliae* NBRC 10307 Strain Using Separation Membrane As an ethanol fermentation microorganism, the *Candida pignaliae* NBRC 10307 strain, which is a yeast having neither vanillin resistance nor acetone resistance, was used to perform continuous fermentation using a separation membrane for 230 hours under the same conditions as in Comparative Example 1, to produce ethanol (Table 5). FIG. 1 shows the remaining sugar concentration in the culture liquid during the preculture, and the remaining sugar concentration in the filtrate from the beginning to the completion of the continuous fermentation using the separation membrane. As a result, we found that, in the continuous fermentation (pH 3) by the *Candida pignaliae* NBRC 10307 strain using the separation membrane, a large amount of sugar that had not been consumed during the continuous fermentation was left unused in the filtrate so that the production efficiency was low.

Comparative Example 3: Production of Ethanol by Continuous Fermentation (pH 3) by *Pichia mexicana* NBRC 10320 Strain Using Separation Membrane As an ethanol fermentation microorganism, the *Pichia mexicana* NBRC 10320 strain, which is not a vanillin-resistant yeast, but is an acetone-resistant yeast, was used to perform continuous fermentation using a separation membrane for 215 hours under the same conditions as in Comparative Example 1, to produce ethanol (Table 5). FIG. 1 shows the remaining sugar concentration in the culture liquid during the preculture, and the remaining sugar concentration in the filtrate from the beginning to the completion of the continuous fermentation using the separation membrane. As a result, we found that, in the continuous fermentation (pH 3) by the *Pichia mexicana* NBRC 10320 strain using the separation membrane, a large amount of sugar that had not been consumed during the continuous fermentation was left unused in the filtrate so that the production efficiency was low. We found that, to reduce the remaining sugar and to produce a chemical product efficiently under the conditions of continuous fermentation (pH 3) using the separation membrane, use of a strain having vanillin resistance is necessary.

Example 1: Production of Ethanol by Continuous Fermentation (pH 3) by *Saccharomyces cerevisiae* NBRC 2260 Strain Using Separation Membrane As an ethanol fermentation microorganism, the *Saccharomyces cerevisiae* NBRC 2260 strain, which is a vanillin-resistant as well as acetone-resistant yeast, was used to perform continuous fermentation using a separation membrane for 240 hours under the same conditions as in Comparative Example 1, to produce ethanol (Table 5). FIG. 1 shows the remaining sugar concentration in the culture liquid during the preculture, and the remaining sugar concentration in the filtrate from the beginning to the completion of the continuous fermentation using the separation membrane. As a result, we found that the *Saccharomyces cerevisiae* NBRC 2260 strain can remarkably reduce the remaining sugar from immediately after the start of the continuous fermentation so that ethanol can be efficiently produced.

Example 2: Production of Ethanol by Continuous Fermentation (pH 3) by *Kluyveromyces marxianus* NBRC 272 Strain Using Separation Membrane As an ethanol fermentation microorganism, the *Kluyveromyces marxianus* NBRC 272 strain, which is a vanillin-resistant as well as acetone-resistant yeast, was used to perform continuous fermentation using a separation membrane for 220 hours under the same conditions as in Comparative Example 1, to produce ethanol (Table 5). FIG. 1 shows the remaining sugar concentration in the culture liquid during the preculture, and the remaining sugar concentration in the filtrate from the beginning to the completion of the continuous fermentation using the separation membrane. As a result, we found that the *Kluyveromyces marxianus* NBRC 272 strain can remarkably reduce the remaining sugar from immediately after the start of the continuous fermentation so that ethanol can be efficiently produced.

Example 3: Production of Ethanol by Continuous Fermentation (pH 3) by *Candida tropicalis* NBRC 199 Strain Using Separation Membrane As an ethanol fermentation microorganism, the *Candida tropicalis* NBRC 199 strain, which is a vanillin-resistant as well as acetone-resistant yeast, was used to perform continuous fermentation using a separation membrane for 250 hours under the same conditions as in Comparative Example 1, to produce ethanol (Table 5). FIG. 1 shows the remaining sugar concentration in the culture liquid during the preculture, and the remaining sugar concentration in the filtrate from the beginning to the completion of the continuous fermentation using the separation membrane. As a result, we found that the *Candida tropicalis* NBRC 199 strain can remarkably reduce the remaining sugar from immediately after the start of the continuous fermentation so that ethanol can be efficiently produced.

Figure 2:
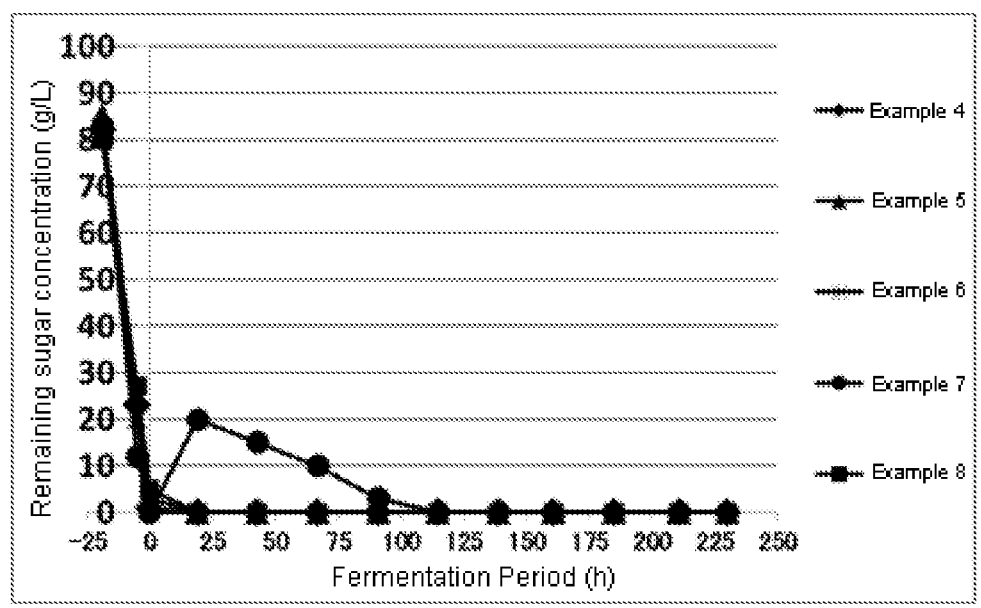
FIG. 2 shows the remaining sugar concentration in the culture liquid during the preculture, and the remaining sugar concentration in the filtrate from the beginning to the completion of the continuous fermentation using a separation membrane, in Examples 4 to 8. Hour 0 represents the time when the continuous fermentation using a separation membrane was started, and the period before Hour 0 corresponds to the preculture period (for 19 hours).

Example 4: Production of Ethanol by Continuous Fermentation (pH 3) by *Arxula adeninivorans* NBRC 10858 Strain Using Separation Membrane As an ethanol fermentation microorganism, the *Arxula adeninivorans* NBRC 10858 strain, which is a vanillin-resistant as well as acetone-resistant yeast, was used to per-form continuous fermentation using a separation membrane for 230 hours under the same conditions as in Comparative Example 1, to produce ethanol (Table 5). FIG. 2 shows the re-maining sugar concentration in the culture liquid during the preculture, and the remaining sugar concentration in the filtrate from the beginning to the completion of the continuous fer-mentation using the separation membrane. As a result, we found that the *Arxula adeninivorans* NBRC 10858 strain can remarkably reduce the remaining sugar from immediately after the start of the continuous fermentation so that ethanol can be efficiently produced.

Example 5: Production of Ethanol by Continuous Fermentation (pH 3) by *Lindnera fabianii* NBRC 1253 Strain Using Separation Membrane As an ethanol fermentation microorganism, the *Lindnera fabianii* NBRC 1253 strain, which is a vanillin-resistant as well as acetone-resistant yeast, was used to perform continuous fermentation using a separation membrane for 230 hours under the same conditions as in Comparative Example 1, to produce ethanol (Table 5). FIG. 2 shows the remaining sugar concentration in the culture liquid during the preculture, and the remaining sugar concentration in the filtrate from the beginning to the completion of the continuous fermentation using the separation membrane. As a result, we found that the *Lindnera fabianii* NBRC 1253 strain can remarkably reduce the remaining sugar from immediately after the start of the continuous fermentation so that ethanol can be efficiently produced.

Example 6: Production of Ethanol by Continuous Fermentation (pH 3) by *Candida methanosorbosa* BCRC 21489 Strain Using Separation Membrane As an ethanol fermentation microorganism, the *Candida methanosorbosa* BCRC 21489 strain, which is a vanillin-resistant as well as acetone-resistant yeast, was used to perform continuous fermentation using a separation membrane for 230 hours under the same conditions as in Comparative Example 1, to produce ethanol (Table 5). FIG. 2 shows the remaining sugar concentration in the culture liquid during the preculture, and the remaining sugar concentration in the filtrate from the beginning to the completion of the continuous fermentation using the separation membrane. As a result, we found that the *Candida methanosorbosa* BCRC 21489 strain, having vanillin resistance as well as acetone resistance, can remarkably reduce the remaining sugar from immediately after the start of the continuous fermentation so that ethanol can be efficiently produced.

Example 7: Production of Ethanol by Continuous Fermentation (pH 3) by *Pichia stipitis* BCRC 21777 Strain Using Separation Membrane As an ethanol fermentation microorganism, the *Pichia stipitis* BCRC 21777 strain, which is a vanillin-resistant yeast, but not an acetone-resistant yeast, was used to perform continuous fermentation using a separation membrane for 230 hours under the same condi-tions as in Comparative Example 1, to produce ethanol (Table 5). FIG. 2 shows the remaining sugar concentration in the culture liquid during the preculture, and the remaining sugar con-centration in the filtrate from the beginning to the completion of the continuous fermentation using the separation membrane. As a result, the *Pichia stipitis* BCRC 21777 showed remaining sugar in the filtrate immediately after the start of the continuous fermentation, but, as the continuous fermentation proceeded, remaining of the sugar could be remarkably suppressed so that this strain was found to be capable of efficiently producing ethanol.

Example 8: Production of Ethanol by Continuous Fermentation (pH 3) by *Candida boidinii* BCRC 22528 Strain Using Separation Membrane As an ethanol fermentation microorganism, the *Candida boidinii* BCRC 22528 strain, which is a vanillin-resistant as well as acetone-resistant yeast, was used to perform continuous fermentation using a separation membrane for 230 hours under the same conditions as in Comparative Example 1, to produce ethanol (Table 5). FIG. 2 shows the remaining sugar concentration in the culture liquid during the preculture, and the remaining sugar concentration in the filtrate from the beginning to the completion of the continuous fermentation using the separation membrane. As a result, we found that the *Candida boidinii* BCRC 22528 strain can remarkably reduce the remaining sugar from immediately after the start of the continuous fermentation so that ethanol can be efficiently produced.

TABLE 5

Ethanol fermentation results 2 (continuous fermentation using a membrane, pH 3)

|  | Comparative Example 1 | Comparative Example 2 | Comparative Example 3 | Example 1 | Example 2 | Example 3 |
|---|---|---|---|---|---|---|
| Culture period (hr) | 250 | 230 | 215 | 240 | 220 | 250 |
| Total amount of glucose fed (g) | 4583 | 4217 | 3942 | 4400 | 4033 | 4583 |
| Total production of ethanol (g) | 1146 | 1081 | 707 | 1892 | 1693 | 1925 |
| Unused glucose (g) | 1719 | 1581 | 2217 | 1 | 2 | 0.8 |
| Yield (g/g) | 0.4 | 0.41 | 0.41 | 0.43 | 0.42 | 0.42 |

|  | Example 4 | Example 5 | Example 6 | Example 7 | Example 8 |
|---|---|---|---|---|---|
| Culture period (hr) | 230 | 230 | 230 | 230 | 230 |
| Total amount of glucose fed (g) | 4217 | 4217 | 4217 | 4217 | 4217 |
| Total production of ethanol (g) | 1770 | 1812 | 1771 | 1660 | 1728 |
| Unused glucose (g) | 2 | 1 | 2 | 264 | 2 |
| Yield (g/g) | 0.42 | 0.43 | 0.42 | 0.42 | 0.41 |

Reference Example 32: Production of Ethanol by Continuous Fermentation (pH 5) by *Saccharomyces cerevisiae* NBRC 10505 Strain Using Separation Membrane As an ethanol fermentation microorganism, the *Saccharomyces cerevisiae* NBRC 10505 strain, which is a yeast having neither vanillin resistance nor acetone resistance, was used to perform continuous fermentation using a separation membrane for 200 hours under the same conditions as in Comparative Example 1 except that the pH was not adjusted to 3 before the inoculation and that the pH was adjusted to 5, to produce ethanol (Table 6). As a result, we found that, in the continuous fermentation (pH 5) by the *Saccharomyces cerevisiae* NBRC 10505 strain using the separation membrane, ethanol can be efficiently produced.

Reference Example 33: Production of Ethanol by Continuous Fermentation (pH 5) by *Saccharomyces cerevisiae* NBRC 2260 Strain Using Separation Membrane As an ethanol fermentation microorganism, the *Saccharomyces cerevisiae* NBRC 2260 strain, which is a vanillin-resistant as well as acetone-resistant yeast, was used to perform continuous fermentation using a separation membrane for 210 hours under the same conditions as in Comparative Example 1 except that the pH was not adjusted to 3 before the inoculation and that the pH was adjusted to 5, to produce ethanol (Table 6). As a result, we confirmed that the *Saccharomyces cerevisiae* NBRC 2260 strain can efficiently produce ethanol.

TABLE 6

Ethanol fermentation results 3
(continuous fermentation using a membrane, pH 5)

|  | Reference Example 32 | Reference Example 33 |
|---|---|---|
| Culture period (hr) | 200 | 210 |
| Total amount of glucose fed (g) | 3667 | 3850 |
| Total production of ethanol (g) | 1540 | 1655 |
| Unused glucose (g) | 1 | 1 |
| Yield (g/g) | 0.42 | 0.43 |

Reference Example 34: Production of Lactic Acid by Batch Fermentation (pH 3) by *Saccharomyces cerevisiae* NBRC 10505/ΔPDC1::LDH Strain As a lactic acid fermentation microorganism, the *Saccharomyces cerevisiae* NBRC 10505/ΔPDC1::LDH strain, which is a yeast having neither vanillin resistance nor acetone resistance, was used to perform batch fermentation under the same conditions as in Reference Example 21, to produce lactic acid (Table 7). As a result, we confirmed that, in the batch fermentation (pH 3) by the *Saccharomyces cerevisiae* NBRC 10505/ΔPDC1::LDH strain, lactic acid can be produced without leaving sugar unused.

Reference Example 35: Production of Lactic Acid by Batch Fermentation (pH 3) by *Saccharomyces cerevisiae* NBRC 2260/ΔPDC1::LDH Strain As a lactic acid fermentation microorganism, the *Saccharomyces cerevisiae* NBRC 2260/ΔPDC1::LDH strain, which is a vanillin-resistant as well as acetone-resistant yeast, was used to perform batch fermentation under the same conditions as in Reference Example 21, to produce lactic acid (Table 7). As a result, we confirmed that, in the batch fermentation (pH 3) by the *Saccharomyces cerevisiae* NBRC 2260/ΔPDC1::LDH strain, lactic acid can be produced without leaving sugar unused.

Reference Example 36: Production of Lactic Acid by Batch Fermentation (pH 3) by *Saccharomyces cerevisiae* NITE BP-1087 Strain As a lactic acid fermentation microorganism, the *Saccharomyces cerevisiae* NITE BP-1087 strain, which is a yeast having neither vanillin resistance nor acetone resistance, was used to perform batch fermentation under the same conditions as in Reference Example 21, to produce lactic acid (Table 8). As a result, we confirmed that, in the batch fermentation (pH 3) by the *Saccharomyces cerevisiae* NITE BP-1087 strain, lactic acid can be produced without leaving sugar unused.

Reference Example 37: Production of Lactic Acid by Batch Fermentation (pH 3) by *Saccharomyces cerevisiae* NITE BP-1088 Strain As a lactic acid fermentation microorganism, the *Saccharomyces cerevisiae* NITE BP-1088 strain, which is a yeast having neither vanillin resistance nor acetone resistance, was used to perform batch fermentation under the same conditions as in Reference Example 21, to produce lactic acid (Table 8). As a result, we confirmed that, in the batch fermentation (pH 3) by the *Saccharomyces cerevisiae* NITE BP-1088 strain, lactic acid can be produced without leaving sugar unused.

Reference Example 38: Production of Lactic Acid by Batch Fermentation (pH 3) by *Saccharomyces cerevisiae* NITE BP-1089 Strain As a lactic acid fermentation microorganism, the *Saccharomyces cerevisiae* NITE BP-1089 strain, which is a yeast having neither vanillin resistance nor acetone resistance, was used to perform batch fermentation under the same conditions as in Reference Example 21, to produce lactic acid (Table 8). As a result, we confirmed that, in the batch fermentation (pH 3) by the *Saccharomyces cerevisiae* NITE BP-1089 strain, lactic acid can be produced without leaving sugar unused.

Comparative Example 4: Production of Lactic Acid by Continuous Fermentation (pH 3) by *Saccharomyces cerevisiae* NBRC 10505/ΔPDC1::LDH Strain Using Separation Membrane As a lactic acid fermentation microorganism, the *Saccharomyces cerevisiae* NBRC 10505/ΔPDC1::LDH strain, which is a yeast having neither vanillin resistance nor acetone resistance, was used to perform continuous fermentation using a separation membrane for 190 hours under the same conditions as in Comparative Example 1, to produce lactic acid (Table 7). As a result, we found that, in the continuous fermentation (pH 3) by the *Saccharomyces cerevisiae* NBRC 10505/ΔPDC1::LDH strain using the separation membrane, there is unused sugar so that the production efficiency is low.

Example 9: Production of Lactic Acid by Continuous Fermentation (pH 3) by *Saccharomyces cerevisiae* NBRC 2260/ΔPDC1::LDH Strain Using Separation Membrane As a lactic acid fermentation microorganism, the *Saccharomyces cerevisiae* NBRC 2260/ΔPDC1::LDH strain, which is a vanillin-resistant as well as acetone-resistant yeast, was used to perform continuous fermentation using a separation membrane for 200 hours under the same conditions as in Comparative Example 1 except that 5 N Ca(OH)$_2$ was used for the pH adjustment for the preculture, to produce lactic acid (Table 7). FIG. 4 shows the remaining sugar concentration in the culture liquid during the preculture, and the remaining sugar concentration in the filtrate from the beginning to the completion of the continuous fermentation using the separation membrane. As a result, we found that the *Saccharomyces cerevisiae* NBRC 2260/ΔPDC1::LDH strain can remarkably reduce the remaining sugar from immediately after the start of the continuous fermentation so that lactic acid can be efficiently produced.

Comparative Example 5: Production of Lactic Acid by Continuous Fermentation (pH 3) by *Saccharomyces cerevisiae* NITE BP-1087 Strain Using Separation Membrane As a lactic acid fermentation microorganism, the *Saccharomyces cerevisiae* NITE BP-1087 strain, which is a yeast having neither vanillin resistance nor acetone resistance, was used to perform continuous fermentation using a separation membrane for 190 hours under the same conditions as in Comparative Example 1, to produce lactic acid (Table 8). As a result, it was found that, in the continuous fermentation (pH 3) by the *Saccharomyces cerevisiae* NITE BP-1087 strain using the separation membrane, there is unused sugar so that the production efficiency is low. That is, we found that, even with a low-pH-resistant yeast, the remaining sugar in the continuous fermentation (pH 3) using the separation membrane cannot be reduced if the yeast does not have vanillin resistance so that lactic acid cannot be efficiently produced.

Comparative Example 6: Production of Lactic Acid by Continuous Fermentation (pH 3) by *Saccharomyces cerevisiae* NITE BP-1088 Strain Using Separation Membrane As a lactic acid fermentation microorganism, the *Saccharomyces cerevisiae* NITE BP-1088 strain, which is a yeast having neither vanillin resistance nor acetone resistance, was used to perform continuous fermentation using a separation membrane for 200 hours under the same conditions as in Comparative Example 1, to produce lactic acid (Table 8). As a result, it was found that, in the continuous fermentation (pH 3) by the *Saccharomyces cerevisiae* NITE BP-1088 strain using the separation membrane, there is unused sugar so that the production efficiency is low. That is, we found that, even with a low-pH-resistant yeast, remaining of the sugar cannot be suppressed in the continuous fermentation (pH 3) using the separation membrane if the yeast does not have vanillin resistance so that lactic acid cannot be efficiently produced.

Comparative Example 7: Production of Lactic Acid by Continuous Fermentation (pH 3) by *Saccharomyces cerevisiae* NITE BP-1089 Strain Using Separation Membrane As a lactic acid fermentation microorganism, the *Saccharomyces cerevisiae* NITE BP-1089 strain, which is a yeast having neither vanillin resistance nor acetone resistance, was used to perform continuous fermentation using a separation membrane for 210 hours under the same conditions as in Comparative Example 1, to produce lactic acid (Table 8). As a result, we found that, in the continuous fermentation (pH 3) by the *Saccharomyces cerevisiae* NITE BP-1089 strain using the separation membrane, there is unused sugar so that the production efficiency is low. That is, it was found that, even with a low-pH-resistant yeast, the remaining sugar in the continuous fermentation (pH 3) using the separation membrane cannot be suppressed if the yeast does not have vanillin resistance so that lactic acid cannot be efficiently produced.

TABLE 7

Lactic acid fermentation results 2
(batch fermentation, continuous fermentation using a membrane, pH 3)

|  | Reference Example 34 | Reference Example 35 | Comparative Example 4 | Example 9 |
|---|---|---|---|---|
| Culture period (hr) | 24 | 15 | 190 | 200 |
| Total amount of glucose fed (g) | 80 | 80 | 3483 | 3667 |
| Total production of lactic acid (g) | 10 | 11 | 627 | 1100 |
| Unused glucose (g) | 0 | 0 | 871 | 1 |
| Yield (g/g) | 0.12 | 0.13 | 0.24 | 0.30 |

TABLE 8

Lactic acid fermentation results 1 (batch fermentation, continuous fermentation using a membrane, pH 3)

|  | Reference Example 36 | Reference Example 37 | Reference Example 38 | Comparative Example 5 | Comparative Example 6 | Comparative Example 7 |
|---|---|---|---|---|---|---|
| Culture period (hr) | 23 | 24 | 23 | 190 | 200 | 210 |
| Total amount of glucose fed (g) | 80 | 80 | 80 | 3483 | 3667 | 3850 |
| Total production of lactic acid (g) | 36 | 30 | 28 | 1385 | 1183 | 1213 |
| Unused glucose (g) | 0 | 0 | 0 | 871 | 917 | 963 |
| Yield (g/g) | 0.45 | 0.37 | 0.35 | 0.53 | 0.43 | 0.42 |

Reference Example 39: Production of Ethanol by Batch Fermentation (pH 3.5) by *Saccharomyces cerevisiae* NBRC 10505 Strain As an ethanol fermentation microorganism, the *Saccharomyces cerevisiae* NBRC 10505 strain, which is a yeast having neither vanillin resistance nor acetone resistance, was used to perform batch fermentation under the same conditions as in Reference Example 37 except that the pH was adjusted to 3.5, to produce ethanol (Table 9). As a result, we confirmed that, in the batch fermentation (pH 3.5) by the *Saccharomyces cerevisiae* NBRC 10505 strain, ethanol can be produced without leaving sugar unused.

Reference Example 40: Production of Ethanol by Batch Fermentation (pH 3.5) by *Saccharomyces cerevisiae* NBRC 2260 Strain As an ethanol fermentation microorganism, the *Saccharomyces cerevisiae* NBRC 2260 strain, which is a vanillin-resistant as well as acetone-resistant yeast, was used to perform batch fermentation under the same conditions as in Reference Example 37 except that the pH was adjusted to 3.5, to produce ethanol (Table 9). As a result, we confirmed that, in the batch fermentation (pH 3.5) by the *Saccharomyces cerevisiae* NBRC 2260 strain, ethanol can be produced without leaving sugar unused.

Comparative Example 8: Production of Ethanol by Continuous Fermentation (pH 3.5) by *Saccharomyces cerevisiae* NBRC 10505 Strain Using Separation Membrane As an ethanol fermentation microorganism, the *Saccharomyces cerevisiae* NBRC 10505 strain, which is a yeast having neither vanillin resistance nor acetone resistance, was used to perform continuous fermentation using a separation membrane for 225 hours under the same conditions as in Comparative Example 1 except that the pH was adjusted to 3.5, to produce ethanol (Table 9). As a result, we found that, in the continuous fermentation (pH 3.5) by the *Saccharomyces cerevisiae* NBRC 10505 strain using the separation membrane, there is unused sugar so that the production efficiency is low.

Example 10: Production of Ethanol by Continuous Fermentation (pH 3.5) by *Saccharomyces cerevisiae* NBRC 2260 Strain Using Separation Membrane As an ethanol fermentation microorganism, the *Saccharomyces cerevisiae* NBRC 2260 strain, which is a vanillin-resistant as well as acetone-resistant yeast, was used to perform continuous fermentation using a separation membrane for 260 hours under the same conditions as in Comparative Example 1 except that the pH was adjusted to 3.5, to produce ethanol (Table 9). As a result, we found that the remaining sugar can be remarkably reduced so that ethanol can be efficiently produced.

TABLE 9

Ethanol fermentation results 4
(batch fermentation, continuous fermentation using a membrane, pH 3.5)

|  | Reference Example 39 | Reference Example 40 | Comparative Example 8 | Example 10 |
|---|---|---|---|---|
| Culture period (hr) | 21 | 15 | 225 | 260 |
| Total amount of glucose fed (g) | 80 | 80 | 4125 | 4767 |
| Total production of ethanol (g) | 33 | 33 | 1429 | 2049 |
| Unused glucose (g) | 0 | 0 | 722 | 1 |
| Yield (g/g) | 0.41 | 0.41 | 0.41 | 0.43 |

Comparative Example 9: Production of Ethanol by Continuous Fermentation (pH 3; Sugar Feed Rate, 2 g/(L·Hr)) by *Saccharomyces cerevisiae* NBRC 10505 Strain Using Separation Membrane As an ethanol fermentation microorganism, the *Saccharomyces cerevisiae* NBRC 10505 strain, which is a yeast having neither vanillin resistance nor acetone resistance, was used to perform continuous fermentation using a separation membrane for 190 hours under the same conditions as in Comparative Example 1 except that the removal rate was 0.9 L/day, and that the sugar feed rate was 2 g/(L·hr), to produce ethanol (Table 10). As a result, we found that, in the continuous fermentation by the *Saccharomyces cerevisiae* NBRC 10505 strain using the separation membrane (sugar feed rate, 2 g/(L·hr)), there is unused sugar so that the production efficiency is low.

Comparative Example 10: Production of Ethanol by Continuous Fermentation (pH 3; Sugar Feed Rate, 4 g/(L·hr)) by *Saccharomyces cerevisiae* NBRC 10505 Strain Using Separation Membrane As an ethanol fermentation microorganism, the *Saccharomyces cerevisiae* NBRC 10505 strain, which is a yeast having neither vanillin resistance nor acetone resistance, was used to perform continuous fermentation using a separation membrane for 200 hours under the same conditions as in Comparative Example 1 except that the removal rate was 1.8 L/day, and that the sugar feed rate was 4 g/(L·hr), to produce ethanol (Table 10). As a result, we found that, in the continuous fermentation by the *Saccharomyces cerevisiae* NBRC 10505 strain using the separation membrane (sugar feed rate, 4 g/(L·hr)), there is unused sugar so that the production efficiency is low.

Comparative Example 11: Production of Ethanol by Continuous Fermentation (pH 3; Sugar Feed Rate, 5 g/(L·hr)) by *Saccharomyces cerevisiae* NBRC 10505 Strain Using Separation Membrane As an ethanol fermentation microorganism, the *Saccharomyces cerevisiae* NBRC 10505 strain, which is a yeast having neither vanillin resistance nor acetone resistance, was used to perform continuous fermentation using a separation membrane for 210 hours under the same conditions as in Comparative Example 1 except that the removal rate was 2.25 L/day, and that the sugar feed rate was 5 g/(L·hr), to produce ethanol (Table 10). As a result, we found that, in the continuous fermentation by the *Saccharomyces cerevisiae* NBRC 10505 strain using the separation membrane (sugar feed rate, 5 g/(L·hr)), there is unused sugar so that the production efficiency is low.

Comparative Example 12: Production of Ethanol by Continuous Fermentation (pH 3; Sugar Feed Rate, 8 g/(L·hr)) by *Saccharomyces cerevisiae* NBRC 10505 Strain Using Separation Membrane As an ethanol fermentation microorganism, the *Saccharomyces cerevisiae* NBRC 10505 strain, which is a yeast having neither vanillin resistance nor acetone resistance, was used to perform continuous fermentation using a separation membrane for 190 hours under the same conditions as in Comparative Example 1 except that the removal rate was 3.6 L/day, and that the sugar feed rate was 8 g/(L·hr), to produce ethanol (Table 10). As a result, we found that, in the continuous fermentation by the *Saccharomyces cerevisiae* NBRC 10505 strain using the separation membrane (sugar feed rate, 8 g/(L·hr)), there is unused sugar so that the production efficiency is low.

Comparative Example 13: Production of Ethanol by Continuous Fermentation (pH 3; Sugar Feed Rate, 10 g/(L·hr)) by *Saccharomyces cerevisiae* NBRC 10505 Strain Using Separation Membrane As an ethanol fermentation microorganism, the *Saccharomyces cerevisiae* NBRC 10505 strain, which is a yeast having neither vanillin resistance nor acetone resistance, was used to perform continuous fermentation using a separation membrane for 200 hours under the same conditions as in Comparative Example 1 except that the removal rate was 4.5 L/day, and that the sugar feed rate was 10 g/(L·hr), to produce ethanol (Table 10). As a result, we found that, in the continuous fermentation by the *Saccharomyces cerevisiae* NBRC 10505 strain using the separation membrane (sugar feed rate, 10 g/(L·hr)), there is unused sugar so that the production efficiency is low.

TABLE 10

Ethanol fermentation results 5
(continuous fermentation using a membrane, pH 3)

|  | Comparative Example 9 | Comparative Example 10 | Comparative Example 11 | Comparative Example 12 | Comparative Example 13 |
|---|---|---|---|---|---|
| Culture period (hr) | 190 | 200 | 210 | 190 | 200 |
| Total amount of glucose fed (g) | 570 | 1200 | 1575 | 2280 | 3000 |
| Total production of ethanol (g) | 219 | 394 | 449 | 627 | 780 |
| Unused glucose (g) | 36 | 240 | 453 | 713 | 1050 |
| Yield (g/g) | 0.41 | 0.41 | 0.4 | 0.40 | 0.4 |
| Sugar Feed Rate (g/(L · hr)) | 2 | 4 | 5 | 8 | 10 |
| Unused glucose/total amount of liquid filtered (g/L) | 5 | 16 | 23 | 25 | 28 |

Example 11: Production of Ethanol by Continuous Fermentation (pH 3; Sugar Feed Rate, 2 g/(L·hr)) by *Saccharomyces cerevisiae* NBRC 2260 Strain Using Separation Membrane As an ethanol fermentation microorganism, the *Saccharomyces cerevisiae* NBRC 2260 strain, which is a vanillin-resistant as well as acetone-resistant yeast, was used to perform continuous fermentation using a separation membrane for 195 hours under the same conditions as in Comparative Example 1 except that the removal rate was 0.9 L/day, and that the sugar feed rate was 2 g/(L·hr), to produce ethanol (Table 11). As a result, we found that the *Saccharomyces cerevisiae* NBRC 2260 strain can remarkably reduce the remaining sugar so that ethanol can be efficiently produced.

Example 12: Production of Ethanol by Continuous Fermentation (pH 3; Sugar Feed Rate, 4 g/(L·hr)) by *Saccharomyces cerevisiae* NBRC 2260 Strain Using Separation Membrane As an ethanol fermentation microorganism, the *Saccharomyces cerevisiae* NBRC 2260 strain, which is a vanillin-resistant as well as acetone-resistant yeast, was used to perform continuous fermentation using a separation membrane for 195 hours under the same conditions as in Comparative Example 1 except that the removal rate was 1.8 L/day, and that the sugar feed rate was 4 g/(L·hr), to produce ethanol (Table 11). As a result, we found that the remaining sugar can be remarkably reduced so that ethanol can be efficiently produced.

Example 13: Production of Ethanol by Continuous Fermentation (pH 3; Sugar Feed Rate, 5 g/(L·hr)) by *Saccharomyces cerevisiae* NBRC 2260 Strain Using Separation Membrane As an ethanol fermentation microorganism, the *Saccharomyces cerevisiae* NBRC 2260 strain, which is a vanillin-resistant as well as acetone-resistant yeast, was used to perform continuous fermentation using a separation membrane for 210 hours under the same conditions as in Comparative Example 1 except that the removal rate was 2.25 L/day, and that the sugar feed rate was 5 g/(L·hr), to produce ethanol (Table 11). As a result, we found that the remaining sugar can be remarkably reduced so that ethanol can be efficiently produced.

Example 14: Production of Ethanol by Continuous Fermentation (pH 3; Sugar Feed Rate, 8 g/(L·hr)) by *Saccharomyces cerevisiae* NBRC 2260 Strain Using Separation Membrane As an ethanol fermentation microorganism, the *Saccharomyces cerevisiae* NBRC 2260 strain, which is a vanillin-resistant as well as acetone-resistant yeast, was used to perform continuous fermentation using a separation membrane for 195 hours under the same conditions as in Comparative Example 1 except that the removal rate was 3.6 L/day, and that the sugar feed rate was 8 g/(L·hr), to produce ethanol (Table 11). As a result, we found that the remaining sugar can be remarkably reduced so that ethanol can be efficiently produced.

Example 15: Production of Ethanol by Continuous Fermentation (pH 3; Sugar Feed Rate, 10 g/(L·hr)) by *Saccharomyces cerevisiae* NBRC 2260 Strain Using Separation Membrane As an ethanol fermentation microorganism, the *Saccharomyces cerevisiae* NBRC 2260 strain, which is a vanillin-resistant as well as acetone-resistant yeast, was used to perform continuous fermentation using a separation membrane for 205 hours under the same conditions as in Comparative Example 1 except that the removal rate was 4.5 L/day, and that the sugar feed rate was 10 g/(L·hr), to produce ethanol (Table 11). As a result, we found that the remaining sugar can be remarkably reduced so that ethanol can be efficiently produced.

TABLE 11

Ethanol fermentation results 6 (continuous fermentation using a membrane, pH 3)

| | Example 11 | Example 12 | Example 13 | Example 14 | Example 15 |
|---|---|---|---|---|---|
| Culture period (hr) | 195 | 195 | 210 | 195 | 205 |
| Total amount of glucose fed (g) | 585 | 1170 | 1575 | 2340 | 3075 |
| Total production of ethanol (g) | 245 | 491 | 677 | 1006 | 1321 |
| Unused glucose (g) | 1 | 1 | 1 | 1 | 2 |
| Yield (g/g) | 0.42 | 0.42 | 0.43 | 0.43 | 0.43 |
| Sugar Feed Rate (g/(L·hr)) | 2 | 4 | 5 | 8 | 10 |
| Unused glucose/total amount of liquid filtered (g/L) | 0 | 0 | 0 | 0 | 0 |

INDUSTRIAL APPLICABILITY

The efficiencies of fermentation production of various chemical products can be improved in continuous fermentation using a separation membrane under low pH conditions, without leaving a large amount of sugar unused.

The invention claimed is:

1. A method of producing a chemical product comprising filtering a culture liquid of yeast through a separation membrane while retaining or refluxing unfiltered liquid in said culture liquid, and adding a fermentation feedstock to said culture liquid to form a culture medium, to perform continuous fermentation under conditions at a pH of not more than 3.5,
    wherein said yeast has vanillin resistance activity characterized by an absorbance at 600 nm of culture liquid obtained by culture of said yeast under Conditions (a) of not less than 20% of an absorbance at 600 nm of culture liquid obtained by culture of said yeast under Conditions (b) and said yeast reduces remaining sugar in a filtrate compared to a yeast without vanillin resistance activity:
        Conditions (a): 40 hours of culture in YPAD medium containing vanillin (final concentration, 1 g/L) (absorbance at 600 nm at the beginning of the culture, 0.2);
        Conditions (b): culture under the same conditions as in Conditions (a) except that the YPAD medium does not contain vanillin,
    said yeast is selected from the group consisting of *Saccharomyces cerevisiae*, *Kluyveromyces marxianus*, *Candida tropicalis*, *Arxula adeninivorans*, *Lindnera fabianii*, *Candida methanosorbosa*, *Pichia stipitis*, and *Candida boidinii*, and
    the culture medium in which the continuous fermentation is performed is tolerable by said yeast without vanillin resistance activity.

2. The method according to claim 1, wherein said yeast has vanillin resistance activity characterized by the absorbance at 600 nm of culture liquid obtained by culture of said yeast under the Conditions (a) of not less than 50% of the absorbance at 600 nm of a culture liquid obtained by culture of said yeast under the Conditions (b).

3. The method according to claim 1, wherein a feed rate of said fermentation feedstock is not less than 4 g/(L·hr).

4. The method according to claim 1, wherein said chemical product is an organic acid or an alcohol.

5. The method according to claim 2, wherein a feed rate of said fermentation feedstock is not less than 4 g/(L·hr).

6. The method according to claim 2, wherein said chemical product is an organic acid or an alcohol.

7. The method according to claim 3, wherein said chemical product is an organic acid or an alcohol.

* * * * *